(12) United States Patent
Klar et al.

(10) Patent No.: US 7,074,829 B2
(45) Date of Patent: *Jul. 11, 2006

(54) ANTIESTROGENS, PROCESS FOR THEIR PRODUCTION AND THEIR PHARMACEUTICAL USE

(75) Inventors: Ulrich Klar, Berlin (DE); Rolf Bohlmann, Berlin (DE); Karsten Parczyk, Berlin (DE); Karl-Heinrich Fritzemeier, Berlin (DE); Monika Lessl, Berlin (DE); Rosemarie Lichtner, Berlin (DE)

(73) Assignee: Schering AG, Berlin (DE)

( * ) Notice: Subject to any disclaimer, the term of this patent is extended or adjusted under 35 U.S.C. 154(b) by 302 days.

This patent is subject to a terminal disclaimer.

(21) Appl. No.: 10/369,577

(22) Filed: Feb. 21, 2003

(65) Prior Publication Data

US 2003/0162830 A1 Aug. 28, 2003

Related U.S. Application Data

(62) Division of application No. 09/706,806, filed on Nov. 7, 2000, now Pat. No. 6,559,181, which is a continuation of application No. 09/328,451, filed on Jun. 9, 1999, now Pat. No. 6,166,075.

(30) Foreign Application Priority Data

Jun. 9, 1998 (DE) .......................... 198 26 213

(51) Int. Cl.
*A01N 37/02* (2006.01)

(52) U.S. Cl. .................. 514/546; 514/708; 514/709; 514/718; 514/724; 549/545; 560/254; 568/27; 568/28; 568/633; 568/715

(58) Field of Classification Search ................. 514/546, 514/708, 709, 718, 724, 727; 549/545; 560/254; 568/27, 28, 633, 715
See application file for complete search history.

(56) References Cited

U.S. PATENT DOCUMENTS

| | | | | | |
|---|---|---|---|---|---|
| 4,133,814 | A | * | 1/1979 | Jones et al. ................ | 548/525 |
| 5,994,371 | A | * | 11/1999 | Black et al. ................ | 514/324 |
| 6,166,075 | A | * | 12/2000 | Klar et al. ................. | 514/546 |

FOREIGN PATENT DOCUMENTS

WO    WO 9313123    8/1993

OTHER PUBLICATIONS

Swift R. "Inhibition of melanoma . . . " CA 126:851112 (1997).*
Zajchowski et al. "Identification of selective . . . " CA 133:144887 (2000).*
Guzi et al. "Preparation of substituted . . . " CA 138:255252 (2003).*
J. Lu et al., "Antioestrogenic activity of two 11beta–oestradiol derivatives on MCF-7 breast cancer cells," *Steroids: Structure, Function And Regulation*, vol. 60, No. 8, Aug. 1, 1995, pp. 512–518.
Aumann et al., "Steroid–Like Ring Skeletons by Cyclohexadiene Annulation to Enamines with Alkynlcarbene Complexes of Chromium and Tungsten via Pyran–2–ylidene Complexes," *J. Am. Chem. Soc.*, No. 118, pp. 10853–10861.

* cited by examiner

*Primary Examiner*—Celia Chang
(74) *Attorney, Agent, or Firm*—Millen, White, Zelano, Branigan, P.C.

(57) ABSTRACT

This invention relates to new antiestrogens of the general formula in which the substituents have the meanings that are explained in more detail in the description.

The new compounds are a) pure antiestrogens or b) antiestrogens with partial estrogenic action (tissue-selective estrogens).

Based on these properties, the new compounds are suitable for the production of pharmaceutical agents: in the case of a), for example, for the treatment of breast cancer; in the case of b), for example, for hormone replacement therapy.

16 Claims, No Drawings

ANTIESTROGENS, PROCESS FOR THEIR PRODUCTION AND THEIR PHARMACEUTICAL USE

This application is a divisional of U.S. Ser. No. 09/706,806 filed Nov. 7, 2000, now U.S. Pat. No. 6,559,181, which is a continuation of U.S. Ser. No. 09/328,451, now U.S. Pat. No. 6,166,075, which are incorporated by reference in their entirety herein.

SUMMARY OF THE INVENTION

This invention relates to 3,4-diphenyl-bicyclo[4.3.0] nonyl derivatives of general formula I

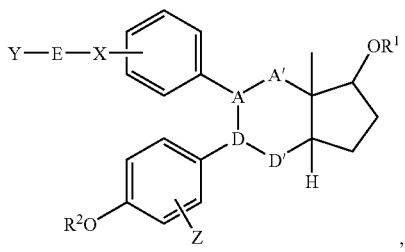

in which

R$^1$ stands for optionally substituted C$_1$–C$_{20}$ alkanoyl, optionally substituted C$_1$–C$_{20}$ alkyl, optionally substituted C$_7$–C$_{20}$ aralkyl, optionally substituted C$_7$–C$_{15}$ aroyl, a group PG$^1$ or a hydrogen atom, R$^2$ stands for optionally substituted C$_1$–C$_{20}$ alkanoyl, optionally substituted C$_1$–C$_{20}$ alkyl, optionally substituted C$_7$–C$_{20}$ aralkyl, optionally substituted C$_7$-C$_{15}$ aroyl, a group PG$^2$ or a hydrogen atom, PG$^1$, PG$^2$ are the same or different and stand for a protective group PG, A'—A—D—D' stands for a —CH$_2$—C(OH)—C═CH—, —CH═C—C(OH)—CH$_2$—, —CH═C—C═CH—, —CH$_2$—C═C—CH$_2$—, —CH$_2$—C(OH)—CH—CH$_2$—, —CH$_2$—CH—C(OH)—CH$_2$—, —CH$_2$—C(OH)—C(OH)—CH$_2$— or

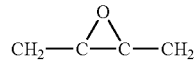

group (hydroxy=α or β; epoxy=α or β),

X stands for a bond, an oxygen atom, a sulfur atom, SO or SO$_2$,

E stands for a straight-chain or branched-chain alkylene, alkenylene or alkynylene group with up to 15 carbon atoms, Y stands for halogen (F, Cl, Br, I), for a substituent R$^4$, an optionally substituted aryl or heteroaryl radical, an NR$^{4a}$R$^{4b}$—, SO$_2$NR$^{4a}$R$^{4b}$—, NR$^{4a}$(CH$_2$)$_p$—Q—G—, NR$^5$(CHR$^6$—CHR$^7$)—(CH$_2$)$_t$—Q—G—, SO$_2$NR$^{4a}$(CH$_2$)$_p$—Q—G—, an O—G—, S—G—, SO—G—, SO$_2$—G group, R$^4$ stands for a hydrogen atom, optionally substituted C$_1$–C$_{20}$ alkyl, partially or completely fluorinated C$_1$–C$_{20}$ alkyl, optionally substituted C$_1$–C$_{20}$ alkanoyl, optionally substituted aryl, optionally substituted heteroaryl, optionally substituted C$_7$–C$_{20}$ aralkyl, optionally substituted C$_7$–C$_{15}$ aroyl, Q stands for an oxygen atom, a sulfur atom, SO or SO$_2$ G stands for —(CH$_2$)$_n$—R$^3$, n stands for 0 to 10, p stands for 1 to 10, t stands for 0, 1 or 2

R$^3$ stands for hydrogen, a straight-chain or branched-chain alkyl, alkenyl or alkynyl group with up to 10 carbon atoms, a straight-chain or branched-chain, partially or completely fluorinated alkyl or alkenyl group with up to 10 carbon atoms, an optionally substituted C$_4$–C$_8$ cycloalkyl group, an optionally substituted aryl group, an optionally substituted C$_7$–C$_{20}$ aralkyl group or, if n>0, also for a hydroxy group or a halogen atom, R$^{4a}$, R$^{4b}$ are the same or different in the meaning of R$^4$ or together stand for a C$_3$–C$_{15}$ alkylene group, which can be straight-chain or branched, R$^5$ means a hydrogen atom or a C$_{1-5}$ alkyl group, R$^6$ and R$^7$ each mean a hydrogen atom, or R$^5$ and R$^6$ together mean an alkylene group —(CH$_2$)$_d$— with d=2, 3, 4 or 5 and R$^7$ is a hydrogen atom or R$^5$ and R$^7$ together mean an alkylene group —(CH$_2$)$_e$— with e=2, 3 or 4 and R$^6$ means a hydrogen atom, Z stands for hydrogen, halogen, OH, N$_3$, NH$_2$, CO$_2$H, CO$_2$—(C$_1$–C$_{20}$)-alkyl, C$_1$–C$_{20}$ alkoxy, —NO$_2$, —CN or C$_1$–C$_{20}$ acyloxy.

As used throughout this application (e.g., with respect to Y, R$^4$ or R$^5$ groups as defined above), the term heteroaryl means, e.g., a C$_4$–C$_{10}$ ring which optionally contains one or more (e.g., 1–3) N, S or O atoms in place of C. Also, as used throughout (e.g., with respect to substituents E, R$^3$, R$^{4a}$ or R$^5$ as defined above), an alkenyene or alkynylene typically contains 1–3 unsaturated bonds.

The invention relates to the diastereomers and/or enantiomers of these derivatives and also their mixtures.

As alkyl groups R$^1$, R$^2$, R$^3$ and R$^4$, straight-chain or branched-chain alkyl groups with up to 20 carbon atoms can be considered, such as, for example, methyl, ethyl, propyl, isopropyl, butyl, isobutyl, tert-butyl, pentyl, isopentyl, neopentyl, heptyl, hexyl and decyl.

Alkyl groups R$^1$, R$^2$, R$^3$ and R$^4$ can be fluorinated partially or completely or substituted by 1–10 halogen atoms, hydroxy groups, C$_1$–C$_4$ alkoxy groups, C$_6$–C$_{12}$ aryl groups, which can be substituted by 1–3 halogen atoms, di-(C$_1$–C$_4$)-alkylamines and tri-(C$_1$–C$_4$)-alkylammonium.

A straight-chain or branched-chain, partially or completely fluorinated alkyl group is preferably the trifluoromethyl or pentafluoroethyl group.

As cycloalkyl groups R$^3$, substituted and unsubstituted radicals with 4 to 8 carbon atoms are considered.

As aryl radicals R$^3$ and R$^4$, substituted and unsubstituted carbocyclic or heterocyclic radicals, such as, e.g., phenyl, naphthyl, furyl, thienyl, pyridyl, pyrazolyl, pyrimidinyl, oxazolyl, pyridazinyl, pyrazinyl, quinolyl, which can be substituted several times by halogen, OH, C$_1$–C$_{20}$ alkoxy, CO$_2$H, CO$_2$ alkyl, —NO$_2$, —N$_3$, —CN, C$_1$–C$_{20}$ alkyl, C$_1$–C$_{20}$ acyl, C$_1$–C$_{20}$ acyloxy groups and defined groups are suitable. As used throughout this application, acyl can be, e.g., alkanoyl.

The alkanoyl groups that are contained in R$^1$, R$^2$ and R$^4$ of general formula I are to contain 1 to 20 carbon atoms in each case, whereby formyl, acetyl, propionyl and isopropionyl groups are preferred.

The aralkyl groups in R$^1$, R$^2$, R$^3$ and R$^4$ can contain in the ring up to 14 C atoms, preferably 6 to 10 C atoms, and in the alkyl chain 1 to 8, preferably 1 to 4 atoms. As aralkyl radicals, for example, benzyl, phenylethyl, naphthylmethyl, naphthylethyl, furylmethyl, thienylethyl, and pyridylpropyl are considered. The rings can be substituted in one or more places by halogen, OH, O-alkyl, CO$_2$H, CO$_2$ alkyl, —NO$_2$, —N$_3$, —CN, C$_1$–C$_{20}$ alkyl, C$_1$–C$_{20}$ acyl, C$_1$–C$_{20}$ acyloxy groups.

As aroyl radicals for $R^1$, $R^2$ and $R^4$, benzoates and benzoates that are substituted in the phenyl radical are to be preferred.

Free hydroxy groups in 1 can be modified functionally, for example by etherification or esterification; free hydroxy groups are preferred, however.

As ether, acyl radicals and protective group PG, the radicals that are known to one skilled in the art, such as, e.g., methoxymethyl, methoxyethyl, ethoxyethyl, tetrahydropyranyl, tetrahydrofuranyl, trimethylsilyl, triethylsilyl, tert-butyldimethylsilyl-, tert-butyldiphenylsilyl, tribenzylsilyl, triisopropylsilyl, methyl, tert-butyl, benzyl, para-nitrobenzyl, para-methoxybenzyl, formyl, acetyl, propionyl, isopropionyl, butyryl, pivalyl, and benzoyl radicals are suitable. A survey is found in, e.g., "Protective Groups in Organic Synthesis," Theodora W. Green, John Wiley and Sons).

As specific side chains, in which X stands for an oxygen atom, there can be mentioned

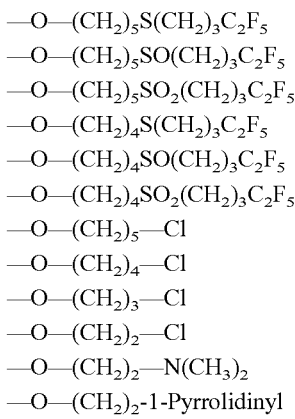

As side chains in which X stands for a direct bond, for example, the following are considered (DE 1 98 06 357.1)

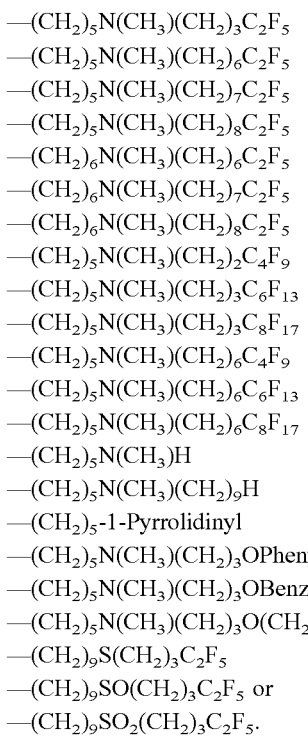

In addition, the side chains of general partial formula

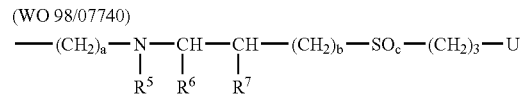

can also be considered,
wherein
a is 4, 5 or 6,
b is 0, 1 or 2,
c is 0, 1 or 2,
$R^5$ is a hydrogen atom or a $C_{1-5}$ alkyl group,
$R^6$ and $R^7$ are each a hydrogen atom, or
$R^5$ and $R^6$ together are an alkylene group $—(CH_2)_d—$ with d=2, 3, 4 or 5, and $R^7$ is a hydrogen atom or
$R^5$ and $R^7$ together are an alkylene group $—(CH_2)_e—$ with e=2, 3 or 4, and $R^6$ is a hydrogen atom, and
U is an unsubstituted ethyl radical or an ethyl radical that is fluorinated in one to five places, or the terminal substituent $—(CH_2)_3—U$ in the side chain is replaced by an optionally substituted aryl or heteroaryl radical, which is bonded to the sulfur atom directly or via a mono-, di- or trimethylene group,
and of the latter in turn especially the side chains
$—(CH_2)_5N(CH_3)(CH_2)_3S(CH_2)_3C_2F_5$ and
$—(CH_2)_5N(R^5)(CHR^6)CH_2S(CH_2)_3C_2F_5$ with $R^5+R^6=—(CH_2)_3—$.

Specific compounds of general formula I are described in the examples.

In addition to these compounds of general formula I, if a nitrogen atom is contained in Y, this invention also relates to their physiologically compatible addition salts with organic and inorganic acids, these compounds of general formula I including the pharmaceutical preparations that contain addition salts as well as their use for the production of pharmaceutical agents.

For the formation of acid addition salts, inorganic and organic acids are suitable, as they are known to one skilled in the art for the formation of physiologically compatible salts. As addition salts with acids, especially hydrochlorides, hydrobromides, acetates, citrates, oxalates, tartrates and methanesulfonates can be mentioned.

The compounds of general formula I represent compounds with strong antiestrogenic action.

The compounds according to the invention are either pure antiestrogens or so-called partial antagonists, i.e., antiestrogens with partial estrogenic action, such as tamoxifen or raloxifene. In contrast to tamoxifen, in the case of the partial antagonists of general formula I, their agonistic estrogenic action manifests itself in a tissue-selective manner. In particular, the agonistic action manifests itself on bone, in the cardiovascular system and in the CNS (central nervous system). In particular, little or no agonistic action manifests itself in the uterus.

Compounds with antiestrogenic properties, i.e., substances with inhibiting actions compared to estrogens, have already been described extensively.

Antiestrogenically active compounds with a 3,4-diphenyl-bicyclo[4.3.0]nonyl-skeleton that can be compared to the existing compounds do not yet exist, however.

The tamoxifen, (Z)-2-[4-(1,2-diphenyl-1-butenyl)-phenoxy]-N,N-dimethylethylamine that can be seen for the first time from BE 637,389 has been used for breast cancer therapy for longer than antiestrogen.

The steroid derivative 7α-[9-(4,4,5,5,5-pentafluoropentylsulfinyl)-n-nonyl]-estra-1,3,5(10)-triene- 3,17β-diol (EP A 0 138 504, page 58, penultimate compound) that can be seen from EP A 0 138 504 B1 is currently under clinical development for hormone-dependent tumors (breast cancer).

Pharmaceutical compositions that contain sex steroid inhibitors, which are a steroidal skeleton, which has a 7α-side chain with the simultaneous presence of at least one other substituent in 14-, 15- or 16-position, are the subject of EP-A 0 376 576.

A considerable number of the most varied compounds— i.a., those of steroidal origin as well as those with a 2-phenylindole skeleton—which act as antiestrogens and/or which suppress estrogen biosynthesis, are disclosed in WO 93/10741.

Other steroidal antiestrogens, which have an 11β-phenyl radical, are described in EP-AS 0 384 842 and 0 629 635.

The uterus growth test in infant rats, p.o. (test on antiestrogenic action in vivo) confirms the antiestrogenic action of the compounds according to the invention. The test can be performed as described below:

Uterus Growth Test in Infant Rats (Antiestrogenic Action)

Principle of the Method

In rodents, the uterus reacts to the administration of estrogens with an increase of weight (both proliferation and water retention). This growth can be inhibited, depending on the dose, by simultaneous administration of compounds that have an antiestrogenic action.

Execution of the Test

Animals:

Infant female rats that weighed 35–45 g at the beginning of the test, 5–6 animals per dose.

Formulation and Administration of Substances:

For p.o. administration, the substances are dissolved in 1 part ethanol (E) and made up with 9 parts peanut oil (EÖ).

Test Preparation

The young rats just dropped by the mothers are delivered for acclimation one day before the beginning of treatment and immediately supplied with food—right in the cage.

The treatment is then carried out once daily over 3 days in combination with 0.5 μg of estradiol benzoate (EB). EB is always administered subcutaneously (s.c.), while the test substance is administered p.o. (perorally). 24 hours after the last administration, the animals are weighed, sacrificed, and the uteri are removed. The moist weight (less contents) is determined from the prepared uteri.

Controls

Negative control: vehicle (E/EÖ), 0.2 ml/animal/day

Positive control: 0.5 μg of EB/0.1 ml/animal/day

Evaluation

Of the relative organ weights (mg/100 g of body weight), the average values with standard deviation (X+SD) and the significance of the differences to the control group (EB) in the Dunnett test (p<0.05) are determined for each group. The calculation of inhibition (in %) compared to the EB control is carried out with a program. The relative levels of effectiveness of the test substances are determined by a co-variance and regression analysis.

| Antiuterotrophic Action in Rats | |
|---|---|
| Compound of Example | Antiuterotrophic Action at 0.3 mg s.c. [% Inhibition] |
| 5 | 55 |
| 3 | 37 |

The compounds according to the invention, especially if they are pure antiestrogens, are suitable for the therapy of estrogen-dependent diseases, such as, for example, breast cancer (second-line therapy of tamoxifen-resistant breast cancer, for adjuvant treatment of breast cancer instead of tamoxifen), endometrial carcinoma, prostate cancer, prostate hyperplasia, anovulatory infertility and melanoma.

In addition, the pure antiestrogens of general formula I can be used as components in the products that are described in EP 346 014 B1, which contain an estrogen and a pure antiestrogen, specifically for simultaneous, sequential or separate use for the selective estrogen therapy of peri- or -post-menopausal women.

The compounds of general formula I, especially if these are pure antiestrogens, can be used together with antigestagens (competitive progesterone antagonists) for the treatment of hormone-dependent tumors (EP 310 542 A).

Other indications, in which the compounds of the general formula can be used, is male hair loss, diffuse alopecia, an alopecia that is caused by chemotherapy, as well as hirsutism (Hye-Sun Oh and Robert C. Smart, Proc. Natl. Acad. Sci. USA, 93 (1996) 12525–12530).

In addition, the compounds of general formula I can be used for the production of medications for treating endometriosis and endometrial carcinomas.

The compounds of general formula I can also be used for the production of pharmaceutical compositions for male and female birth control (male birth control: DE-A 195 10 862.0).

The compounds of general formula I with tissue-selective partial estrogenic action can be used primarily for prophylaxis and therapy of osteoporosis and for the production of preparations for substitution therapy in pre-, peri- and post-menopause (HRT=hormone replacement therapy) (Black, L. J.; Sato, M.; Rowley, E. R.; Magee, D. E.; Bekele, A.; William, D. C.; Cullinan, G. J.; Bendele, R.; Kauffman, R. F.; Bensch, W. R.; Frolik, C. A.; Termine, J. D. and Bryant, H. U.: Raloxifene [LY 139481 HCl] Prevents Bone Loss and Reduces Serum Cholesterol without Causing Uterine Hypertrophy in Ovariectomized Rats; J. Clin. Invest. 93: 63–69, 1994).

The invention also relates to pharmaceutical preparations that contain at least one compound of general formula I (or physiologically compatible addition salts with organic and inorganic acids thereof) and the use of these compounds for the production of pharmaceutical agents, especially for treating estrogen-dependent diseases and tumors and pharmaceutical agents for hormone replacement therapy (HRT).

The compounds according to the invention and the acid addition salts are suitable for the production of pharmaceutical compositions and preparations. The pharmaceutical compositions or pharmaceutical agents contain as active ingredients one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants and other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullmans' Encyclopedia of Technical Chemistry], Volume 4 (1953), pages 1 to 39; Journal of Pharmaceutical Sciences, Volume 52 (1963), page 918 and ff.; issued by Czetsch-Lindenwald. Hilfsstoffe für Pharmazie und angrenzende Gebiete [Adjuvants for Pharmaceutics and Related Fields]: Pharm. Ind. Issue 2, 1961, page 72 and ff.; Dr. H. P. Fiedler, Lexikon der Hilfsstoffe für Pharmazie, Kosmetik und angrenzende Gebiete [Dictionary of Adjuvants for Pharmaceutics, Cosmetics and Related Fields] Cantor K G, Aulendorf in Württemberg 1971.

The compounds can be administered orally or parenterally, for example intraperitoneally, intramuscularly, subcutaneously or percutaneously. The compounds can also be implanted in the tissue. The amount of the compounds that is to be administered varies within a wide range and can cover any effective amount. On the basis of the condition that is to be treated and the type of administration, the amount of the administered compound is 0.1–25 mg/kg of body weight, preferably 0.5–5 mg/kg of body weight, per day. In humans, this corresponds to a daily dose of 5 to 1250 mg.

The preferred daily dosage in humans is 50 to 200 mg. This holds true especially for tumor therapy.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc. The individual dosage units for oral administration can contain, for example, 5 to 500 mg of the active ingredient.

To achieve better bio-availability of the active ingredient, the compounds can also be formulated as cyclodextrin clathrates. For this purpose, the compounds are reacted with $\alpha$-, $\beta$- or $\gamma$-cyclodextrin or derivatives thereof (PCT/EP95/02656).

According to the invention, the compounds of general formula I can also be encapsulated with liposomes.

For parenteral administration, the active ingredients can be dissolved or suspended in a physiologically compatible diluent. As diluents, very often oils with or without the addition of a solubilizer, a surfactant, a suspending agent or an emulsifier are used. Examples of oils that are used are olive oil, peanut oil, cottonseed oil, soybean oil, castor oil and sesame oil.

The compounds of general formula I can also be formulated in the form of a solution that is intended for oral administration, and that in addition to the active compound of general formula I contains a) a pharmaceutically compatible oil and/or b) a pharmaceutically compatible lipophilic surfactant and/or c) a pharmaceutically compatible hydrophilic surfactant and/or d) a pharmaceutically compatible water-miscible solvent.

In addition, reference is made to WO 97/21440 in this respect.

The compounds can also be used in the form of a depot injection or an implant preparation, which can be formulated in such a way that a delayed release of active ingredient is made possible.

As inert materials, implants can contain, for example, biodegradable polymers or synthetic silicones, such as, for example, silicone gum. In addition, the active ingredients can be embedded in, for example, a patch, for percutaneous administration.

For the production of intravaginal systems (e.g., vaginal rings) or intrauterine systems (e.g., pessaries, coils) that are loaded with active compounds of general formula I, various polymers are suitable, such as, for example, silicon polymers, ethylene vinyl acetate, polyethylene or polypropylene.

The compounds according to the invention can be used alone or to achieve additive or synergistic actions in combination with other principles and classes of substances that can be used in tumor therapy.

As examples, there can be mentioned the combination with

○ Platinum complexes, such as, e.g., cis-platinum, carboplatinum,

○ intercalating substances, e.g., from the class of anthracyclines, such as, e.g., doxorubicin or from the class of anthrapyrazoles, such as, e.g., Cl-941, ○ substances that interact with tubulin, e.g., from the class of vinca-alkaloids, such as, e.g., vincristine, vinblastine or from the class of taxanes, such as, e.g., taxol, taxotere or from the class of macrolides, such as, e.g., rhizoxin and its analogs, epothilone B and its analogs, discodermolide and its analogs, eleutherobine and its analogs, or other compounds, such as, e.g., colchicine, combretastatin A-4, ○ DNA topoisomerase inhibitors, such as, e.g., camptothecin, etoposide, topotecan, teniposide, ○ folate- or pyrimidine-antimetabolites, such as, e.g, lometrexol, gemcitubin, ○ DNA-alkylating compounds, such as, e.g., adozelesin, dystamycin A, ○ inhibitors of growth factors (e.g., of PDGF, EGF, TGFβ, EGF), such as, e.g., somatostatin, suramin, bombesin antagonists, ○ inhibitors of protein tyrosine kinases or protein kinases A or C, such as, e.g., erbstatin, genistein, staurosporine, ilmofosine, 8-Cl-cAMP, ○ antihormones from the class of antigestagens, such as, e.g., mifepristone, onapristone or from the class of antiestrogens, such as, e.g., tamoxifen or from the class of antiandrogens, such as, e.g., cyproterone acetate (combination with antigestagens, see, for example, EP 0 310 542 B1 and EP 0 310 541 B1), ○ metastases-inhibiting compounds, e.g., from the class of eicosanoids, such as, e.g., $PGl_2$, $PGE_1$, 6-oxo-$PGE_1$ as well as their more stable derivatives (e.g., iloprost, cicaprost), ○ inhibitors of oncogenic RAS proteins, which influence the mitotic signal transduction, such as, for example, inhibitors of the farnesyl-protein-transferase, ○ natural or synthetically produced antibodies, which are directed against factors or their receptors, which promote tumor growth, such as, for example, the erbB2 antibody.

The invention also relates to a process for the production of compounds of formula I, which are described in more detail in Diagram 1 below.

Diagram 1

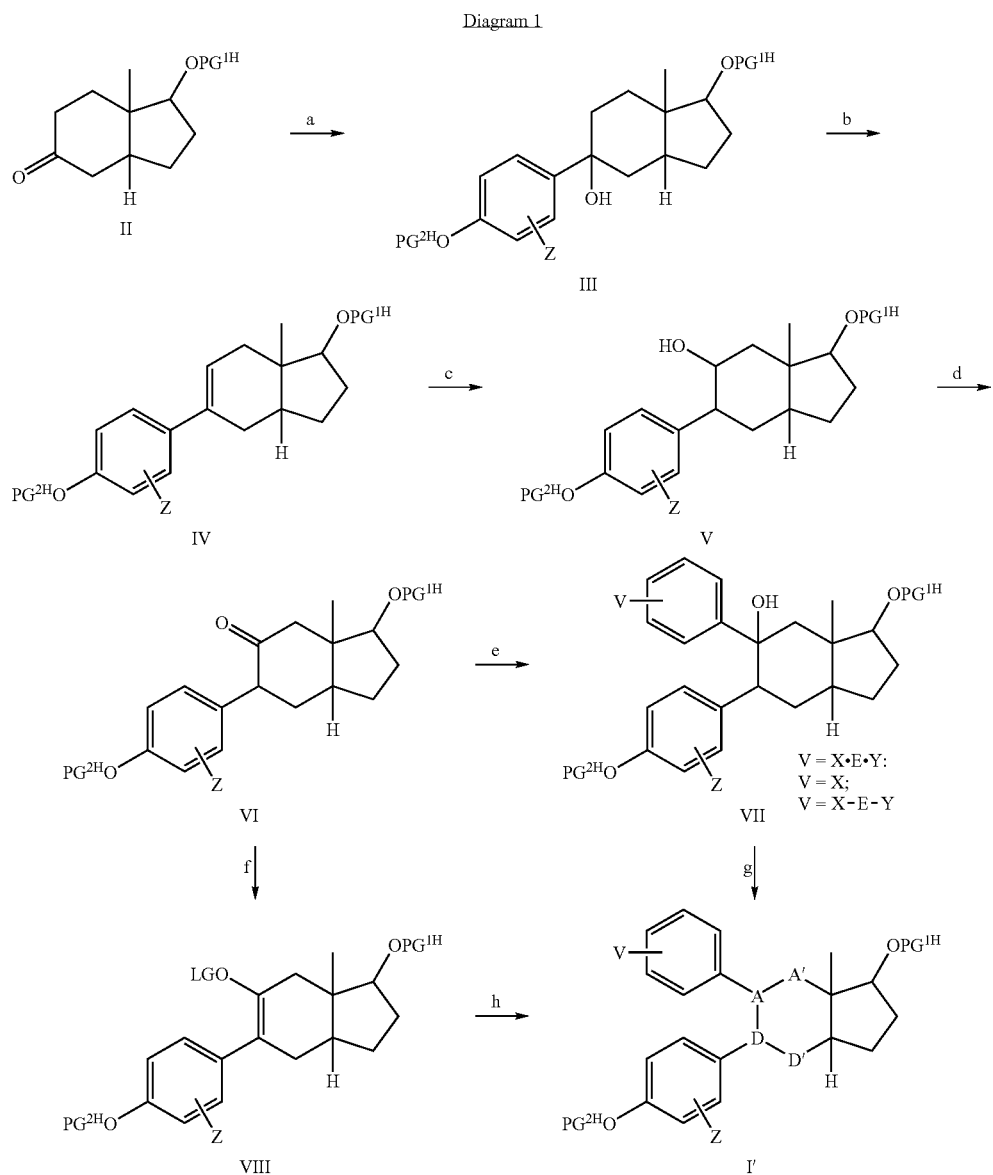

Step a (II→III):

Ketone II, in which $PG^{1H}$ can have the meanings that are mentioned above for $PG^1$ or $PG^{1H}$ means a hydrogen atom, is produced according to processes that are known in the literature. The reaction to an aryl compound of formula III is carried out by reaction with an organometallic compound of general formula

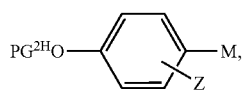

in which M stands for an alkali metal or for a divalent metal atom M-Hal, in which Hal is a halogen atom, $PG^{2H}$ has the meanings that are mentioned above for $PG^2$ and Z or $PG^{2H}$ means a hydrogen atom, and free OH, $CO_2H$ or $NH_2$ groups in Z are optionally protected. As divalent metal, magnesium and zinc are preferred; as halogen, Hal is preferably chlorine, bromine and iodine. The reaction is carried out in an inert solvent, preferably in tetrahydrofuran or diethyl ether. As $PG^{1H}$, hydrogen or a protective group $PG^1$ in the meaning of tert-butyl- or tert-butyldimethylsilyl is preferred; as $PG^{2H}$, hydrogen or a protective group $PG^2$ in the meaning of methyl, benzyl, or tert-butyldimethylsilyl is preferred. A selective modification of protective groups $PG^1$ and/or $PG^2$ is possible.

Step b (III→IV):

The elimination of water in III to olefin IV is carried out according to the methods that are known to one skilled in the art. The use of mineral aqueous acids and inert organic, water-miscible solvents, such as, for example, dioxane or tetrahydrofuran, is preferred. Under these conditions, protective groups $PG^1$ and/or $PG^2$ that can be cleaved acidically are also eliminated. A selective modification of protective groups $PG^1$ and/or $PG^2$ is possible. As $PG^{1H}$, hydrogen or a protective group $PG^1$ in the meaning of tert-butyl- or tert-butyldimethylsilyl is preferred; as $PG^{2H}$, hydrogen or a protective group $PG^2$ in the meaning of benzyl- or tert-butyldimethylsilyl is preferred.

Step c (IV→V):

Water is added to the double bond in IV in an anti-Markovnikov orientation. For this purpose, the processes that are known to one skilled in the art are suitable, such as, e.g., reaction with boranes, their subsequent oxidation to the corresponding boric acid esters and their saponification. As boranes, e.g., the borane-tetrahydrofuran complex, the borane-dimethyl sulfide complex, 9-borabicyclo[3.3.1]nonane in an inert solvent such as, for example, tetrahydrofuran or diethyl ether, are preferred. As oxidizing agents, preferably hydrogen peroxide is used; for saponification of the boron esters, preferably alkali hydroxides, such as, e.g., sodium hydroxide, are used.

Step d (V→VI):

The oxidation of the alcohol in V to ketone is carried out according to the methods that are known to one skilled in the art. For example, oxidation with pyridinium chlorochromate, pyridinium dichromate, chromium trioxide-pyridine complex, oxidation according to Swern or related methods, e.g., with use of oxalyl chloride in dimethyl sulfoxide, the use of Dess-Martin periodinane, the use of nitrogen oxides, such as, e.g., N-methyl-morpholino-N-oxide in the presence of suitable catalysts, such as, e.g., tetrapropylammonium perruthenate in inert solvents, can be mentioned. Preferred is the oxidation with the chromium-trioxide-pyridine complex. A selective modification of protective groups $PG^1$ and/or $PG^2$ is possible. As $PG^{1H}$, hydrogen or a protective group $PG^1$ in the meaning of tetrahydropyranyl or tert-butyldimethylsilyl is preferred; as $PG^{2H}$, hydrogen or a protective group $PG^2$ in the meaning of tetrahydropyranyl, benzyl or tert-butyldimethylsilyl is preferred.

Step e (VI→VII):

The reaction of ketone VI to an aryl compound of formula VII is carried out by reaction with an organometallic compound of general formula

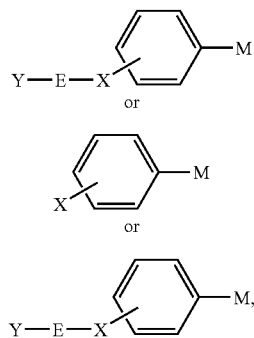

in which M stands for an alkali metal or for a divalent metal atom M-Hal, in which Hal is a halogen atom, and Y, E and X have the above-mentioned meanings; free OH, SH or NH groups are optionally protected in Y; X' stands for a protected hydroxy group OPG, and Y' stands for a group OLG, a halogen atom (F, Cl, Br, I) or a group OPG. As a divalent metal, magnesium and zinc are preferred; as halogen, Hal is preferably chlorine, bromine and iodine. The reaction is carried out in an inert solvent, preferably in tetrahydrofuran or diethyl ether. A selective modification of Y as well as of protective groups $PG^1$ and/or $PG^2$ is possible. As $PG^{1H}$, hydrogen or a protective group $PG^1$ in the meaning of acetyl, tetrahydropyranyl or tert-butyldimethylsilyl, is preferred; as $PG^{2H}$, hydrogen or a protective group $PG^2$ in the meaning of tetrahydropyranyl, benzyl or tert-butyldimethylsilyl is preferred.

Hydroxyl groups that are released into X' or Y' can be modified further by etherification.

If Y' represents a halogen, preferably Cl, Br, I or a leaving group OLG, the additional chain creation can be carried out by, for example, alkylation, amination (e.g., with $HNR^{4a}R^{4b}$, $HNR^{4a}(CH_2)_p$-Q-G) or etherification (e.g., with HO-G, HS-G).

To create the side chain, reference is otherwise made to the processes and examples that are described in EP A 0 138 504, EP-A 0 376 576, WO 98/07740 and DE 1 98 06 357.1 for the creation of the 7α-side chain of the steroid. By an analogous procedure, the side chains that are described there and synthesized can be created in these compounds as -X-E-Y.

Step f (VI→VIII):

The reaction of ketone VI to an enol compound of formula VIII, in which LG represents a leaving group, is carried out according to the processes that are known to one skilled in the art. By using a strong base in an inert solvent, such as, for example, tetrahydrofuran or diethyl ether, the enolate of ketone VI is generated and then reacted with a compound LG-Hal, in which Hal has the meaning of fluorine, chlorine, bromine or iodine. As leaving group LG, for example, alkylsulfonyls or optionally substituted arylsulfonyls, for example the tosylate radical, are suitable; preferred are perfluorinated alkylsulfonyls, such as, for example, perfluorobutylsulfonyl or trifluoromethylsulfonyl. As $PG^{1H}$, a protective group $PG^1$ in the meaning of tetrahydropyranyl or tert-butyldimethylsilyl is preferred; as $PG^{2H}$, a protective group $PG^2$ in the meaning of tetrahydropyranyl, benzyl or tert-butyldimethylsilyl is preferred.

Step g (VII→I'):

The elimination of water in VII to compounds of formula I' with A—D in the meaning of a C—C double bond is carried out according to the conditions that are mentioned under step b. The double bond can optionally be hydrogenated (A—D in the meaning of a C—C-single bond) or oxidized (A—D in the meaning of a

a COH—CH—, a CH—COH— or a COH—COH group) according to the processes that are known to one skilled in the art. A selective modification of Y as well as of protective groups $PG^1$ and/or $PG^2$ is possible. As $PG^{1H}$, hydrogen or a protective group $PG^1$ in the meaning of acetyl, tetrahydropyranyl or tert-butyldimethylsilyl is preferred; as $PG^{2H}$, hydrogen or a protective group $PG^2$ in the meaning of tetrahydropyranyl, benzyl or tert-butyldimethylsilyl is preferred.

Step h (VIII→I'):

The reaction of compound VIII is carried out according to the methods that are known to one skilled in the art. It is preferably reacted with a boronic acid of formula

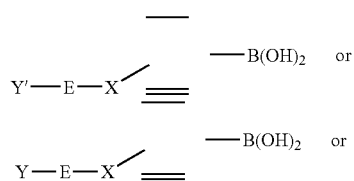

-continued

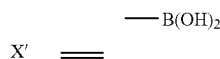

in which Y, E, X, Y' and X' have the above-mentioned meanings, and free OH—, SH— or NH groups are optionally protected in Y, under palladium(O)-catalysis to a compound of formula I' with A—D in the meaning of a C—C double bond. The double bond can optionally be hydrogenated (A—D in the meaning of a C—C single bond) or oxidized (A—D in the meaning of a

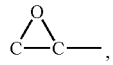

a COH—CH—, a CH—COH— or a COH—COH group) according to the processes that are known to one skilled in the art. A selective modification of Y as well as of protective groups $PG^1$ and/or $PG^2$ is possible. As $PG^{1H}$, hydrogen or a protective group $PG^1$ in the meaning of acetyl, tetrahydropyranyl or tert-butyldimethylsilyl is preferred; as $PG^{2H}$, hydrogen or a protective group $PG^2$ in the meaning of tetrahydropyranyl, benzyl or tert-butyldimethylsilyl is preferred. The cleavage of protective groups that are optionally contained in I' according to the processes that are known to one skilled in the art results in compounds I according to the invention.

The compounds according to the invention can be produced as described below. By an analogous procedure using analogous reagents in the data that is contained in the examples, additional compounds of general formula I can be obtained.

As processes for the creation of side chain -X-E-Y in the compounds according to the invention, especially also methods of side chain introduction and of side chain creation that are described in EP 0 138 504 B1 and EP 0 376 576 A are suitable.

A thio bridge in the side chain can be oxidized with sodium periodate to sulfoxide; the sulfoxides and sulfones are obtained from the sulfides with a peracid as an oxidizing agent, e.g., m-chloroperbenzoic acid.

The saponification of ester groupings as well as esterification and etherification of free hydroxy groups is carried out in each case according to established processes of organic chemistry.

The acid addition salts of the compounds of general formula I can also be produced according to standard processes from the compounds of general formula I.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 198 206 213.2, filed Jun. 9, 1998 is hereby incorporated by reference.

EXAMPLES

Example 1

(1S,3S,4R,6S,9S)-9-Hydroxy-4-(4-hydroxyphenyl)-1-methyl-3-[4-(10,10,11,11,11-pentafluoro-6-thia-undecyloxy)phenyl]-bicyclo[4.3.0]nonane Example 1a (1S,4R,6S,9S)-4-(4-Methoxyphenyl)-4-hydroxy-1-methyl-9-tert-butyloxy-bicyclo[4.3.0]nonane (A) and (1S,4S,6S,9S)-4-(4-methoxyphenyl)-4-hydroxy-1-methyl-9-tert-butyloxy-bicyclo[4.3.0]nonane (B)

Under a dry atmosphere of argon, the suspension that consists of 4.8 g of magnesium chips in 40 ml of anhydrous tetrahydrofuran is mixed with 0.2 ml of 1,2-dibromomethane; 24.6 ml of 4-bromoanisole in 260 ml of tetrahydrofuran is slowly added in drops so that the internal temperature does not exceed 28° C., and stirring is continued for 1 hour at 23° C. Then, it is mixed with the solution of 10.0 g (44.6 mmol) of (1S,6S,9S)-9-tert-butyloxy-1-methyl-bicyclo[4.3.0]nonan-4-one in 100 ml of tetrahydrofuran and stirred for 16 hours at 23° C. At 0° C., it is mixed with saturated ammonium chloride solution, diluted with water and ethyl acetate, the organic phase is separated, washed with saturated sodium chloride solution and dried on sodium sulfate. The residue that is obtained after filtration and removal of the solvent is purified by chromatography on about 1.5 l of fine silica gel with a gradient system that consists of n-hexane and ethyl acetate. 5.45 g (16.4 mmol, 37%) of title compound A and 8.16 g (24.5 mmol, 55%) of title compound B are isolated in each case as a colorless foam.

$^1$H-NMR (CDCl$_3$) of A: δ=0.82 (3H), 1.16 (9H), 1.30–1.73 (8H), 1.78–2.06 (4H), 3.53 (1H), 3.80 (3H), 6.88 (2H), 7.43 (2H) ppm.

$^1$H-NMR (CDCl$_3$) of B: δ=0.90 (3H), 1.08 (9H), 1.13 (1H), 1.28–1.60 (4H), 1.68–1.89 (4H), 2.00 (1H), 2.22 (1H), 2.35 (1H), 3.26 (1H), 3.82 (3H,), 6.91 (2H), 7.50 (2H) ppm.

Example 1b (1S,4S,6S,9S)-4-(4-Hydroxyphenyl)-9-tert-butyloxy-4-hydroxy-1-methyl-bicyclo[4.3.0]nonane Analogously to Example 1c, 8.16 g (24.5 mmol) of compound B that is presented according to Example 1a is reacted, and the crude product that is obtained after working-up is purified together with the crude product that is obtained in Example 1c.

Example 1c (1S,6S,9S)-4-(4-Hydroxyphenyl)-9-tert-butyloxy-1-methyl-bicyclo[4.3.0]non-3-ene (A) and (1S,4R,6S,9S)-4-(4-hydroxyphenyl)-9-tert-butyloxy-4-hydroxy-1-methyl-bicyclo[4.3.0]nonane (B)

The solution of 5.45 g (16.4 mmol) of compound A, presented according to Example 1a, in 70 ml of anhydrous dimethylformamide is mixed under an atmosphere of dry argon with 5.65 g of sodium methanethiolate, and it is heated for about 5 hours to 170° C. After cooling, it is poured into water, extracted several times with ethyl acetate, the combined organic extracts are washed with saturated sodium chloride solution and dried on sodium sulfate. The residue that is obtained after filtration and removal of the solvent is combined with the crude product that is obtained in Example 1b and purified by chromatography on about 800 ml of fine silica gel with a gradient system that consists of n-hexane and ethyl acetate. 8.00 g (26.6 mmol, 65% relative to products A and B that are obtained in Example 1a) of title compound A and 1.85 g (5.81 mmol, 14% relative to products A and B that are obtained in Example 1a) of title compound B are isolated in each case as a colorless foam.

$^1$H-NMR (CDCl$_3$+CD$_3$OD) of A: δ=0.72 (3H), 1.14 (9H), 1.33–1.74 (4H), 1.83–2.03 (2H), 2.03–2.21 (2H), 2.26-2.54 (2H), 3.52 (1H), 5.91 (1H), 6.72 (2H), 7.23 (2H) ppm.

$^1$H-NMR (CDCl$_3$+CD$_3$OD) of B: δ=0.78 (3H), 1.14 (9H), 1.20–2.01 (13H), 3.51 (1H), 6.76 (2H), 7.30 (2H) ppm.

Example 1d (1S,6S,9S)-4-(4-Benzyloxyphenyl)-9-tert-butyloxy-1-methyl-bicyclo[4.3.0]non-3-ene and (1S,4R,6S,9S)-4-(4-benzyloxyphenyl)-9-tert-butyloxy-4-hydroxy-1-methyl-bicyclo[4.3.0]nonane 1.85 g (5.81 mmol) of compound B that is presented according to Example 1c is treated analogously to Example 1e, and the crude mixture, which contains the title compounds, is further reacted without purification.

Example 1e (1S,6S,9S)-4-(4-Benzyloxyphenyl)-9-tert-butyloxy-1-methyl-bicyclo[4.3.0]non-3-ene 8.0 g (26.6 mmol) of compound A that is presented according to Example 1c is mixed with 80 ml of a 50% potassium hydroxide solution, 32 ml of benzyl chloride and 1 g of tetrabutyl-ammonium hydrogen sulfate. It is allowed to react for about 4 hours at 50° C. while being stirred vigorously, and the crude mixture, which contains the title compound, is further reacted without purification.

Example 1f (1S,6S,9S)-4-(4-Benzyloxyphenyl)-9-hydroxy-1-methyl-bicyclo[4.3.0]non-3-ene The crude products that are obtained according to Examples 1e and 1d are dissolved in 300 ml of dioxane, mixed with 40 ml of a 4N hydrochloric acid and heated for 16 hours to 80° C. After cooling, it is poured into saturated sodium bicarbonate solution, extracted several times with dichloromethane, the combined organic extracts are washed with saturated sodium chloride solution and dried on sodium sulfate. The residue that is obtained after filtration and removal of the solvent is purified by chromatography on about 1.5 l of fine silica gel with a gradient system that consists of n-hexane and ethyl acetate. 9.35 g (28.0 mmol, 87% relative to products A and B that are obtained in Example 1c) of the title compound is isolated as a colorless foam.

$^1$H-NMR (CDCl$_3$): δ=0.79 (3H), 1.36-1.62 (3H), 1.65–1.83 (2H), 2.01–2.64 (4H), 2.49 (1H), 3.83 (1H), 5.08 (2H), 6.00 (1H), 6.93 (2H), 7.28–7.52 (7H) ppm.

Example 1g (1S,6S,9S)-4-(4-Benzyloxyphenyl)-9-tert-butyldimethylsilyloxy-1-methyl-bicyclo[4.3.0]non-3-ene The solution of 6.81 g (20.36 mmol) of the compound, presented according to Example 1f, in 60 ml of anhydrous dimethylformamide is mixed under an atmosphere of dry argon with 2.42 g of imidazole, 10 ml of tert-butyldimethylchlorosilane, and it is stirred for 16 hours at 23° C. It is poured into water, extracted several times with ethyl acetate, and the combined organic extracts are dried on sodium sulfate. The residue that is obtained after filtration and removal of the solvent is purified by chromatography on about 1 l of fine silica gel with a gradient system that consists of n-hexane and ethyl acetate. 8.71 g (19.4 mmol, 95%) of the title compound is isolated as a colorless foam.

$^1$H-NMR (CDCl$_3$): δ=0.03 (3H), 0.05 (3H), 0.75 (3H), 0.90 (9H), 1.38–1.78 (4H), 1.87–2.27 (4H), 2.46 (1H), 3.73 (1H), 5.07 (2H), 5.97 (1H), 6.92 (2H), 7.28–7.51 (7H) ppm.

Example 1h (1S,3R,4S,6S,9S)-4-(4-Benzyloxyphenyl)-9-tert-butyldimethylsilyloxy-3-hydroxy-1-methyl-bicyclo[4.3.0]nonane The solution of 8.71 g (19.1 mmol) of the compound, presented according to Example 1g, in 225 ml of anhydrous tetrahydrofuran is mixed under an atmosphere of dry argon with 38.5 ml of a 1 molar borane-tetrahydrofuran solution, cooled after 2 hours to 0° C., mixed with 65 ml of a 5% sodium hydroxide solution, then with 30 ml of a 30% hydrogen peroxide solution, and it is stirred for another 30 minutes. It is diluted with water and ethyl acetate, the organic phase is separated, washed with saturated sodium thiosulfate solution and dried on sodium sulfate. The residue that is obtained after filtration and removal of the solvent is purified by chromatography on about 1 l of fine silica gel with a gradient system that consists of n-hexane and ethyl acetate. 8.06 g (17.3 mmol, 90%) of the title compound is isolated as a colorless foam.

$^1$H-NMR (CDCl$_3$): δ=0.03 (3H), 0.05 (3H), 0.88 (3H), 0.90 (9H), 1.12 (1H), 1.25–1.76 (7H), 1.98 (1H), 2.18 (1H), 2.38 (1H), 3.71 (1H), 3.94 (1H), 5.07 (2H), 6.97 (2H), 7.19 (2H), 7.29–7.51 (5H) ppm.

Example 1i (1S,4S,6S,9S)-4-(4-Benzyloxyphenyl)-9-tert-butyldimethylsilyloxy-1-methyl-3-oxo-bicyclo[4.3.0]nonane 12 g of chromium trioxide is mixed at 0° C. with 50 ml of anhydrous dichloromethane and 46 ml of pyridine, it is stirred for 20 minutes, and the compound, presented according to Example 1h, in 50 ml of anhydrous dichloromethane is mixed with the solution of 8.59 g (18.4 mmol). It is allowed to react for 5 hours at 0° C. under an atmosphere of dry argon, poured into a 5% sodium hydroxide solution, the residue is washed with dichloromethane, and the combined organic extracts are washed with saturated sodium chloride solution and dried on sodium sulfate. The residue that is obtained after filtration and removal of the solvent is purified by chromatography on about 1 l of fine silica gel with a gradient system that consists of n-hexane and ethyl acetate. 7.02 g (15.1 mmol, 82%) of the title compound is isolated as a colorless foam.

$^1$H-NMR (CDCl$_3$): δ=0.04 (6H), 0.82 (3H), 0.90 (9H), 1.47 (1H), 1.58 (1H), 1.71 (1H), 1.90 (1H), 1.98–2.19 (3H), 2.23 (1H), 2.57 (1H), 3.40 (1H), 3.89 (1H), 5.06 (2H), 6.96 (2H), 7.03 (2H), 7.28–7.49 (5H) ppm.

Example 1k (1S,3S,4S,6S,9S)-4-(4-Benzyloxyphenyl)-9-tert-butyldimethylsilyloxy-3-hydroxy-1-methyl-3-[4-(5-chloropentyloxy)phenyl]-bicyclo[4.3.0]nonane The solution of 3.91 g of 4-bromo-(5-chloropent-1-oxy)-phenyl in 70 ml of anhydrous tetrahydrofuran is cooled under an atmosphere of dry argon to –78° C., mixed with 4.52 ml of a 2.5 molar solution of n-butyllithium in n-hexane and, after 45 minutes, with the solution of 4.38 g (9.42 mmol) of the compound, presented according to Example 1i, in 70 ml of tetrahydrofuran. After 1.5 hours, the reaction mixture is poured into saturated ammonium chloride solution, extracted several times with ethyl acetate, the combined organic extracts are washed with saturated sodium chloride solution and dried on sodium sulfate. The residue that is obtained after filtration and removal of the solvent is purified by chromatography on about 1 l of fine silica gel with a gradient system that consists of n-hexane and ethyl acetate. 4.00 g (6.03 mmol, 64%) of the title compound and 1.43 g (33%) of starting material are isolated in each case as a colorless foam.

$^1$H-NMR (CDCl$_3$): δ=0.03 (3H), 0.00 (3H), 0.86 (9H), 1.13 (3H), 1.45–2.10 (14H), 2.19 (1H), 3.07 (1H), 3.59 (2H), 3.71 (1H), 3.95 (2H), 4.96 (2H), 6.65–6.81 (6H), 7.12 (2H) 7.28–7.43 (5H) ppm.

Example 11

(1S,6S,9S)-4-(4-Benzyloxyphenyl)-3-[4-(5-chloropentyloxy)-phenyl]-9-hydroxy-1-methyl-bicyclo[4.3.0]non-3-ene The solution of 4.0 g (6.03 mmol) of the compound, presented according to Example 1k, in 70 ml of dioxane is mixed with 9 ml of a 4N hydrochloric acid, and it is heated under argon atmosphere for 16 hours to 80° C. After cooling, it is mixed with saturated sodium bicarbonate solution, extracted several times with dichloromethane, and the combined organic extracts are dried on sodium sulfate. The residue that is obtained after filtration and removal of the solvent is purified by chromatography on about 400 ml of fine silica gel with a gradient system that consists of n-hexane and ethyl acetate. 3.01 g (5.67 mmol, 94%) of the title compound is isolated as a colorless foam.

$^1$H-NMR (CDCl$_3$): δ=0.91 (3H), 1.36–1.68 (5H), 1.68–1.90 (6H), 2.08–2.39 (3H), 2.48 (1H), 2.53 (1H), 3.56 (2H), 3.88 (3H), 4.98 (2H), 6.63 (2H), 6.73 (2H), 6.99 (4H), 7.27–7.46 (5H) ppm.

Example 1m (1S,3S,4R,6S,9S)-3-[4-(5-Chloropentyloxy)phenyl]-9-hydroxy-4-(4-hydroxyphenyl)-1-methyl-bicyclo[4.3.0]nonane The solution of 1.40 g (2.64 mmol) of the compound that is presented according to Example 11 is mixed with 140 mg of palladium on carbon (10%) and hydrogenated while being shaken at 1 atmosphere of hydrogen. It is filtered on Celite, rewashed with dichloromethane, and the residue that is obtained after removal of the solvent is further reacted without purification. 1.17 g (2.64 mmol, 100%) of the title compound is isolated as a colorless foam.

$^1$H-NMR (CDCl$_3$+CD$_3$OD): δ=0.31 (3H), 1.27–1.82 (11H), 1.93–2.14 (3H), 2.34 (1H), 3.08 (1H), 3.49 (2H), 3.60 (1H), 3.69 (1H), 3.80 (2H), 6.53 (2H), 6.65 (2H), 7.00 (2H), 7.12 (2H) ppm.

Example 1

(1S,3S,4R,6S,9S)-9-Hydroxy-4-(4-hydroxyphenyl)-1-methyl-3-[4-(10,10,11,11,11-pentafluoro-6-thia-undecyloxy)phenyl]-bicyclo[4.3.0]nonane The solution of 2.3 g of thioacetic acid-S-(4,4,5,5,5-pentafluoro-pentyl)ester in 90 ml of methanol is mixed under an atmosphere of dry argon with 540 mg of sodium ethanolate, it is allowed to react for 2 hours at 23° C. and heated for another 2 hours to 40° C. It is allowed to cool to 23° C., and the solution of 980 mg (2.21 mmol) of the compound, presented according to Example 1m, in 60 ml of anhydrous methanol is added in drops, mixed with 460 mg of sodium iodide and heated for 16 hours to 80° C. The reaction mixture is poured into water, extracted several times with ethyl acetate, the combined organic extracts are washed with water and saturated sodium chloride solution and dried on sodium sulfate. The residue that is obtained after filtration and removal of the. solvent is purified by chromatography on 200 ml of fine silica gel with a gradient system that consists of n-hexane and ethyl acetate. 901 mg (1.50 mmol, 68%) of the title compound and 300 mg of the starting material are isolated.

Example 2

(1S,3S,4R,6S,9S)-9-Acetyloxy-4-(4-hydroxyphenyl)-1-methyl-3-[4-(10,10,11,11,11-pentafluoro-6-thia-undecyloxy)phenyl]-bicyclo[4.3.0]nonane

Example 2a (1S,6S,9S)-9-Acetyloxy-4-(4-benzyloxyphenyl)-3-[4-(5-chloropentyloxy)phenyl]-1-methyl-bicyclo[4.3.0]non-3-ene 1.50 g (2.82 mmol) of the compound that is presented according to Example 11 is esterified analogously to Example 2d, and after working-up and purification, 1.58 g (2.76 mmol, 98%) of the title compound is isolated as a colorless foam.

Example 2b (1S,3S,4R,6S,9S)-9-Acetyloxy-3-[4-(5-chloropentyloxy)phenyl]-4-(4-hydroxyphenyl)-1-methyl-bicyclo[4.3.0]nonane 1.58 g (2.76 mmol) of the compound that is presented according to Example 2a is reacted analogously to Example 1m, and after working-up, 1.31 g (2.70 mmol, 98%) of the title compound is isolated as a colorless foam, which is further reacted without purification.

$^1$H-NMR (CDCl$_3$): δ=0.43 (3H), 1.40–1.96 (11H), 2.01 (3H), 2.10–2.26 (3H), 2.31 (1H), 3.14 (1H), 3.53 (2H), 3.72 (1H), 3.84 (2H), 4.63 (1H), 4.68 (1H), 6.58 (2H), 6.69 (2H), 7.02 (2H), 7.18 (2H) ppm.

Example 2c (1S,3S,4R,6S,9S)-9-Acetyloxy-3-[4-(5-chloropentyloxy)phenyl]-1-methyl-4-[4-(tetrahydropyran-2-yloxy)phenyl]-bicyclo[4.3.0]nonane The solution of 1.31 g (2.70 mmol) of the compound, presented according to Example 2b, in 35 ml of anhydrous dichloromethane is mixed under an atmosphere of dry argon with 3.3 ml of 3,4-dihydro-(2H)-pyran, 341 mg of p-toluenesulfonic acid-monohydrate, and it is stirred for 4 hours at 23° C. It is poured into saturated sodium bicarbonate solution, extracted several times with dichloromethane, the combined organic extracts are washed with saturated sodium chloride solution and dried on sodium sulfate. The residue that is obtained after filtration and removal of the solvent is purified by chromatography on about 300 ml of fine silica gel with a gradient system that consists of n-hexane and ethyl acetate. 1.13 g (2.51 mmol, 93%) of the title compound is isolated as a colorless foam.

$^1$H-NMR (CDCl$_3$): δ=0.43 (3H), 1.40–2.05 (17H), 2.02 (3H), 2.10–2.25 (3H), 2.31 (1H), 3.16 (1H), 3.54 (3H), 3.74 (1H), 3.83 (2H), 3.89 (1H), 4.63 (1H), 5.32 (1H), 6.59 (2H), 6.91 (2H), 7.03 (2H), 7.22 (2H) ppm.

Example 2d (1S,3S,4R,6S,9S)-9-Acetyloxy-1-methyl-3-[4-(10,10,11,11,11-pentafluoro-6-thia-undecyloxy)phenyl]-4-[4-(tetrahydropyran-2-yloxy)phenyl]-bicyclo[4.3.0]nonane.

The solution of 1.43 g (2.51 mmol) of the compound that is presented in Example 2c is reacted analogously to Example 1, and after working-up, a mixture that consists of the title compound is isolated, and (1S,3S,4R,6S,9S)-9-hydroxy-4-[4-(tetrahydropyran-2-yloxy)phenyl]-1-methyl-3-[4-(10,10,11,11,11-pentafluoro-6-thia-undecyloxy)phenyl]-bicyclo[4.3.0]nonane, which is dissolved in 25 ml of anhydrous pyridine, is mixed with 3 ml of acetic anhydride and a spatula tip full of 4-dimethylaminopyridine, and it is stirred for 2 hours at 23° C. It is poured into saturated sodium bicarbonate solution, extracted several times with dichloromethane, the combined organic extracts are washed with saturated sodium chloride solution-and dried on sodium sulfate. The residue that is obtained after filtration and removal of the solvent is purified by chromatography on about 400 ml of fine silica gel with a gradient system that consists of n-hexane and ethyl acetate. 1.57 g (2.16 mmol, 86%) of the title compound is isolated as a colorless foam.

Example 2

(1S,3S,4R,6S,9S)-9-Acetyloxy-4-(4-hydroxyphenyl)-1-methyl-3-[4-(10,10,11,11,11-pentafluoro-6-thia-undecyloxy)phenyl]-bicyclo [4.3.0]nonane The solution of 1.57 g (2.16 mmol) of the compound, presented according to Example 2d, in 50 ml of anhydrous ethanol is mixed under an atmosphere of dry argon with 400 mg of p-toluenesulfonic acid-monohydrate, and it is stirred for 1 hour at 23° C. It is poured into saturated sodium bicarbonate solution, extracted several times with dichloromethane, the combined organic extracts are washed with saturated sodium chloride solution and dried on sodium sulfate. The residue that is obtained after filtration and removal of the solvent is purified by chromatography on about 300 ml of fine silica gel with a gradient system that consists of n-hexane and ethyl acetate. 1.12 g (1.74 mmol, 81%) of the title compound is isolated as a colorless solid. Crystallization from ethyl acetate yields colorless crystals.

$^1$H-NMR (CDCl$_3$): δ=0.43 (3H), 1.40–1.80 (12H), 1.80–1.95 (3H), 2.01 (3H), 2.04–2.37 (6H), 2.51 (2H), 2.59 (2H), 3.14 (1H), 3.72 (1H), 3.83 (2H), 4.64 (1H), 6.58 (2H), 6.69 (2H), 7.02 (2H), 7.18 (2H) ppm.

Example 3

(1S,3S,4R,6S,9S)-9-Hydroxy-4-(4-hydroxyphenyl)-1-methyl -3-[4-(5-(4,4,5,5,5-pentafluoro-pentylsulfinyl)pentyloxy)phenyl]-bicyclo[4.3.0]nonane The solution of 200 mg (0.330 mmol) of the compound, presented according to Example 1, in 8 ml of dichloromethane is mixed with 0.88 ml of a 0.5 molar sodium bicarbonate solution and 116 mg of 55% meta-chloroperbenzoic acid, and it is stirred for 0.5 hour at 23° C. It is poured into saturated sodium bicarbonate solution, extracted several times with dichloromethane, the combined organic extracts are washed with saturated sodium chloride solution and dried on sodium sulfate. The residue that is obtained after filtration and removal of the solvent is purified by chromatography on about 100 ml of fine silica gel with a gradient system that consists of n-hexane and ethyl acetate. 122 mg (0.20 mmol, 60%) of the title compound is isolated as a colorless foam.

$^1$H-NMR (CDCl$_3$): δ=0.41 (3H), 1.30–1.88 (12H), 2.01–2.32 (7H), 2.39 (1H), 2.55–2.82 (4H), 3.13 (1H), 3.61–3.78 (2H), 3.85 (2H), 5.74+5.83 (1H), 6.56 (2H), 6.68 (2H), 7.01 (2H), 7.16 (2H) ppm.

Example 4

(1S,3S,4R,6S,9S)-9-Hydroxy-4-(4-hydroxyphenyl)-1-methyl-3-[4-(5-(4,4,5,5,5-pentafluoro-pentylsulfonyl)pentyloxy)phenyl]-bicyclo[4.3.0]nonane 174 mg (0.29 mmol) of the compound that is presented according to Example 1 is reacted analogously to Example 3 with use of double the amount of meta-chloroperbenzoic acid and 1.5 hours of reaction time, and after working-up and purification, 136 mg (0.21 mmol, 74%) of the title compound is isolated as a colorless foam.

$^1$H-NMR (CDCl$_3$): δ=0.36 (3H), 1.23–1.97 (12H), 2.01–2.45 (8H), 2.90–3.09 (4H), 3.13 (1H), 3.61–3.79 (2H), 3.85 (2H), 4.79 (1H), 6.57 (2H), 6.69 (2H), 7.03 (2H), 7.19 (2H) ppm.

Example 5

(1S,3S,4R,6S,9S)-9-Acetyloxy-4-(4-hydroxyphenyl-1-methyl-3-[4-(4,4,5,5,5-pentafluoro-pentylsulfinyl)pentyloxy)phenyl-bicyclo[4.3.0]nonane 250 mg (0.389 mmol) of the compound that is presented according to Example 2 is reacted analogously to Example 3, and after working-up and purification, 149 mg (0.226 mmol, 58%) of the title compound is isolated as a colorless foam.

$^1$H-NMR (CDCl$_3$): δ=0.47 (3H), 1.41–1.84 (11H), 1.91 (1H), 2.01 (3H), 2.08–2.33 (7H), 2.55–2.81 (4H), 3.14 (1H), 3.70 (1H), 3.88 (2H), 4.64 (1H), 5.62+5.72 (1H), 6.57 (2H) 6.68 (2H), 7.01 (2H), 7.13 (2H) ppm.

Example 6

(1S,6S,9S)-9-Hydroxy-4-(4-hydroxyphenyl)-1-methyl]-3-[4-(10,10,11,11,11-pentafluoro-6-thia-undecyloxy)phenyl]-bicyclo[4.3.0]non-3-ene

Example 6a (1S,3S,4S,6S,9S)-9-tert-Butyldimethylsilyloxy-3-[4-(5-chloropentyloxy)phenyl]-3-hydroxy-4-(4-hydroxyphenyl)-1-methyl-bicyclo[4.3.0]nonane 9.80 g (14.8 mmol) of the compound that is presented according to Example 1k is reacted analogously to Example 1m, and after working-up and purification, 6.23 g (10.9 mmol, 73%) of the title compound is isolated as a colorless foam.

$^1$H-NMR (CDCl$_3$): δ=0.03 (3H), 0.01 (3H), 0.87 (9H), 1.17 (3H), 1.44–1.73 (9H), 1.74–2.09 (6H), 2.17 (1H), 3.03 (1H), 3.58 (2H), 3.71 (1H), 3.94 (2H), 4.58 (1H), 6.57 (2H) 6.71 (2H), 6.77 (2H), 7.12 (2H) ppm.

Example 6b (1S,6S,9S)-3-[4-(5-Chloropentyloxy)phenyl]-9-hydroxy-4-(4-hydroxyphenyl)-1-methyl-bicyclo [4.3.0]non-3-ene 5.60 g (9.77 mmol) of the compound that is presented according to Example 6a is reacted analogously to Example 1l, and after,working-up and purification, 4.11 g (9.32 mmol, 95%) of the title compound is isolated as a colorless foam.

$^1$H-NMR (CDCl$_3$): δ=0.91 (3H), 1.35–1.68 (5H), 1.68–1.90 (6H), 2.08–2.38 (3H), 2.41–2.58 (2H), 3.54 (2H), 3.89 (3H) 4.77 (1H), 6.57 (2H), 6.62 (2H), 6.82 (2H), 6.87 (2H) ppm.

Example 6

(1S,6S,9S)-9-Hydroxy-4-(4-hydroxyphenyl)-1-methyl-3-[4-(10,10,11,11,11-pentafluoro-6-thia-undecyloxy)phenyl]-bicyclo[4.3.0]non-3-ene 4.11 g (9.32 mmol) of the compound that is presented according to Example 6b is reacted analogously to Example 1, and after working-up and purification, 4.32 g (7.22 mmol, 77%) of the title compound is isolated as a colorless foam.

$^1$H-NMR (CDCl$_3$): δ=0.91 (3H), 1.36–1.97 (13H), 2.07–2.38 (5H), 2.41–2.64 (6H), 3.87 (3H), 4.68 (1H), 6.57 (2H), 6.63 (2H), 6.83 (2H), 6.87 (2H) ppm.

Example 7

(1S,6S,9S)-9-Acetyloxy-4-(4-hydroxyphenyl)-1-methyl-3-[4-(10,10,11,11,11-pentafluoro-6-thia-undecyloxy)phenyl]-bicyclo[4.3.0]non-3-ene

Example 7a (1S,6S,9S)-4-(4-tert-Butyldimethylsilyloxyphenyl)-9-hydroxy-1-methyl-3-[4-(10,10,11,11,11-pentafluoro-6-thia-undecyloxy)phenyl]-bicyclo[4.3.0]non-3-ene The solution of 2.08 g (3.47 mmol) of the compound, presented according to Example 6, in 50 ml of anhydrous tetrahydrofuran is cooled under an atmosphere of dry argon to 0° C., mixed with 157 mg of a 55% sodium hydride dispersion, 1.5 ml of a 3 molar solution of tert-butyldimethylchlorosilane in n-hexane, and it is stirred for 1.5 hours at 23° C. It is poured into water, extracted with ethyl acetate, the organic phase is washed with saturated sodium chloride solution and dried on sodium sulfate. The residue that is obtained after filtration and removal of the solvent is further reacted without purification. 2.7 g (max. 3.47 mmol) of the title compound is isolated.

$^1$H-NMR (CDCl$_3$): δ=0.11 (6H), 0.89 (3H), 0.93 (9H), 1.37–1.93 (13H), 2.03–2.36 (5H), 2.4–2.63 (6H), 3.85 (3H), 6.56 (2H), 6.59 (2H), 6.80 (2H), 6.84 (2H) ppm.

Example 7b (1S,6S,9S)-9-Acetyloxy-4-(4-tert-butyldimethylsilyloxyphenyl)-1-methyl-3-[4-(10,10,11,11,11-pentafluoro-6-thia-undecyloxy)phenyl]-bicyclo[4.3.0]non-3-ene 2.7 g (max. 3.47 mmol) of the compound that is presented according to Example 7a is esterified analogously to Example 2d, and after working-up, 3.0 g of the title compound, which is further reacted without purification, is isolated.

Example 7

(1S,6S,9S)-9-Acetyloxy-4-(4-hydroxyphenyl)-1-methyl-3-[4-(10,10,11,11,11-pentafluoro-6-thia-undecyloxy)phenyl]-bicyclo[4.3.0]non-3-ene The solution of 3.0 g (max. 3.47 mmol) of the compound, presented according to Example 7b, in 200 ml of anhydrous tetrahydrofuran is mixed under an atmosphere of dry argon with 3.5 ml of a 1 molar solution of tetrabutylammonium fluoride in tetrahydrofuran, and it is stirred for 3 hours at 23° C. It is poured into saturated ammonium chloride solution, extracted several times with ethyl acetate, the combined organic extracts are washed with saturated sodium chloride solution and dried on sodium sulfate. The residue that is obtained after filtration and removal of the solvent is purified by chromatography on about 600 ml of fine silica gel with a gradient system that consists of n-hexane and ethyl acetate. 1.87 g (2.92 mmol, 85% relative to the starting material in Example 7a) of the title compound is isolated as a colorless foam.

$^1$H-NMR (CDCl$_3$): δ=0.93 (3H), 1.39–1.97 (12H), 2.02–2.64 (11H), 2.07 (3H), 3.87 (2H), 4.62 (1H), 4.82 (1H), 6.55 (2H), 6.62 (2H), 6.83 (4H) ppm.

Example 8

(1S,6S,9S)-9-Acetyloxy-4-(4-hydroxyphenyl)-1-methyl-3-[4-(5-(4,4,5,5,5-pentafluoro-pentylsulfonyl)pentyloxy)phenyl]-bicyclo[4.3.0]non-3-ene 500 mg (0.78 mmol) of the compound that is presented according to Example 7 is reacted analogously to Example 4, and after working-up and purification, 308 mg (0.46 mmol, 59%) of the title compound is isolated as a colorless foam.

$^1$H-NMR (CDCl$_3$): δ=0.95 (3H), 1.41–1.97 (10H), 2.07 (3H), 2.11–2.43 (8H), 2.51 (1H), 2.92–3.09 (4H), 3.91 (2H), 4.82 (1H), 4.91 (1H), 6.56 (2H), 6.61 (2H), 6.81 (2H), 6.86 (2H) ppm.

Example 9

(1S,6S,9S)-9-Acetyloxy-4-(4-hydroxyphenyl)-1-methyl-3-[4-(5-(4,4,5,5,5-pentafluoro-pentylsulfonyl)pentyloxy)phenyl]-bicyclo[4.3.0]non-3-ene 3.10 mg (0.48 mmol) of the compound that is presented according to Example 7 is reacted analogously to Example 3, and after working-up and purification, 255 mg (0.39 mmol, 80%) of the title compound is isolated as a colorless foam.

$^1$H-NMR (CDCl$_3$): δ=0.95 (3H), 1.40–1.96 (10H), 2.02 (3H), 2.07–2.84 (13H), 3.87–4.02 (2H), 4.81 (1H), 6.55 (2H), 6.61 (2H), 6.77 (2H), 6.83 (2H), 6.93 (1H) ppm.

Example 10

(1S,6S,9S)-9-Hydroxy-4-(4-hydroxyphenyl)-1-methyl-3-[4-(5-(4,4,5,5,5-pentafluoro-pentylsulfonyl)pentyloxy)phenyl]-bicyclo[4.3.0]non-3-ene 500 mg (0.835 mmol) of the compound, presented according to Example 6, is reacted analogously to Example 4, and after working-up and purification, 290 mg (0.46 mmol, 55%) of the title compound is isolated as a colorless foam.

$^1$H-NMR (CDCl$_3$): δ=0.91 (3H), 1.37–1.98 (11H), 2.09–2.53 (9H), 2.92–3.10 (4H), 3.87 (1H), 3.91 (2H), 4.95 (1H), 6.56 (2H), 6.61 (2H), 6.81 (2H), 6.87 (2H) ppm.

Example 11

(1S,2S,4R,6S,9S)-3,4-Epoxy-9-hydroxy-4-(4-hydroxyphenyl)-1-methyl-3-[4-(5-(4,4,5,5,5-pentafluoro-pentylsulfonyl)pentyloxy)phenyl]-bicyclo[4.3.0]nonane 151 mg (0.24 mmol) of the compound that is presented according to Example 10 is reacted analogously to Example 3, and after working-up and purification, 92 mg (0.14 mmol, 59%) of the title compound is isolated as a colorless foam.

$^1$H-NMR (CDCl$_3$): δ=1.12 (3H), 1.40–2.43 (20H), 2.91–3.11 (4H), 3.79 (1H), 3.88 (2H), 5.13 (1H), 6.53 (2H), 6.59 (2H), 6.96 (2H), 7.01 (2H) ppm.

Example 12

(1S,6S,9S)9-Hydroxy-4-(4-hydroxyphenyl)-1-methyl-3-[4-(5-(4,4,5,5,5-pentafluoro-pentylsulfinyl)pentyloxy)phenyl]-bicyclo[4.3.0]non-3-ene 500 mg (0.835 mmol) of the compound, presented according to Example 6, is reacted analogously to Example 3, and after working-up and purification, 357 mg (0.58 mmol, 70%) of the title compound is isolated as a colorless foam.

$^1$H-NMR (CDCl$_3$+CD$_3$OD): δ=0.88 (3H), 1.33–1.85 (9H), 2.01–2.31 (7H), 2.37–2.81 (8H), 3.80 (1H), 3.88 (2H), 6.52 (2H), 6.58 (2H), 6.74 (2H), 6.83 (2H) ppm.

Example 13

(1S,3S,4R,6S,9S)-9-Acetoxy-3,4-epoxy-4-(4-hydroxyphenyl)-1-methyl -3-[4-(5-(4,4,5,5,5-pentafluoro-pentylsulfonyl)pentyloxy)phenyl]-bicyclo[4.3.0]nonane 110 mg (0.16 mmol) of the compound that is presented according to Example 8 is reacted analogously to Example 3, and after working-up and purification, 81 mg (0.12 mmol, 50%) of the title compound is isolated as a colorless foam.

$^1$H-NMR (CDCl$_3$): δ=1.40–2.38 (19H), 2.06 (3H), 2.90–3.08 (4H), 3.89 (2H), 4.71 (1H), 5.08 (1H), 6.63 (2H), 6.59 (2H), 6.97 (2H), 6.99 (2H) ppm.

Example 14

(1S,6S,9S)-9-Hydroxy-4-(4-hydroxyphenyl)-1-methyl-3-[4-(2-chloroethyloxy)phenyl]-bicyclo[4.3.0]non-3-ene Example 14a (1S,6S,9S)-9-Hydroxy-4-(4-hydroxyphenyl)-1-methyl-bicyclo[4.3.0]non-3-ene 12.8 g (42.7 mmol) of compound A, presented according to Example 1a, is reacted analogously to Example 1f, and after working-up and purification, 8.5 g (34.8 mmol, 81%) of the title compound is isolated as a colorless foam.

Example 14b (1S,6S,9S)-9-(tert-Butyldimethylsilyloxy)-4-(4-tert-butyldimethylsilyloxyphenyl)-1-methyl-bicyclo[4.3.0]non-3-ene 8.5 g (34.8 mmol) of the compound that is presented according to Example 14a is reacted analogously to Example 1g, and after working-up and purification, 15.0 g (31.7 mmol, 91%) of the title compound is isolated as a colorless foam.

$^1$H-NMR (CDCl$_3$): δ=0.04 (6H), 0.19 (6H), 0.73 (3H), 0.90 (9H), 0.98 (9H), 1.38–1.78 (4H), 1.87–2.03 (2H), 2.08–2.25 (2H), 2.44 (1H), 3.73 (1H), 5.98 (1H), 6.78 (2H), 7.28 (2H) ppm.

Example 14c (1S,3R,4S,6S,9S)-9-(tert-Butyldimethylsilyloxy)-3-hydroxy-4-(4-tert-butyldimethylsilyloxyphenyl)-1-methyl-bicyclo[4.3.0]nonane 15.0 g (31.7 mmol) of the compound that is presented according to Example 14b is reacted analogously to Example 1h, and after working-up and purification, 14.4 g (29.3 mmol, 93%) of the title compound is isolated as a colorless foam.

$^1$H-NMR (CDCl$_3$): δ=0.03 (6H), 0.19 (6H), 0.87 (3H), 0.89 (9H), 0.99 (9H), 1.12 (1H), 1.22–1.74 (7H), 1.97 (1H), 2.17 (1H), 2.36 (1H), 3.71 (1H), 3.92 (1H), 6.81 (2H), 7.12 (2H) ppm.

Example 14d (1S,4S,6S,9S)-9-(tert-Butyldimethylsilyloxy)-4-(4-tert-butyldimethylsilyloxyphenyl)-1-methyl-3-oxo-bicyclo[4.3.0]nonane 14.4 g (29.3 mmol) of the compound that is presented according to Example 14c is reacted analogously to Example 1i, and after working-up and purification, 9.49 g (19.4 mmol, 66%) of the title compound is isolated as a colorless foam.

$^1$H-NMR (CDCl$_3$): δ=0.03 (6H), 0.19 (6H), 0.79 (3H), 0.88 (9H), 0.97 (9H), 1.44 (1H), 1.55 (1H), 1.69 (1H), 1.87 (1H), 1.96–2.17 (3H), 2.21 (1H), 2.53 (1H), 3.38 (1H), 3.87 (1H) 6.79 (2H), 6.96 (2H) ppm.

Example 14e (1S,6S,9S)-9-(tert-Butyldimethylsilyloxy)-4-(4-tert-butyldimethylsilyloxyphenyl)-1-methyl-3-(nonafluorobutylsulfonyloxy)-bicyclo[4.3.0]non-3-ene The solution of 5.0 g (10.2 mmol) of the compound, presented according to Example 14d, and 3.71 g of potassium-bis-(trimethylsilyl)amide in 95 ml of anhydrous tetrahydrofuran is mixed at 0° C. with 2.42 ml of perfluorobutanesulfonyl fluoride, and it is stirred for 1.5 hours. It is poured onto sodium bicarbonate solution, extracted several times with ethyl acetate, and the combined organic extracts are dried on sodium sulfate. The residue that is obtained after filtration and removal of the solvent is further reacted without purification.

Example 14f (1S,6S,9S)-9-(tert-Butyldimethylsilyloxy)-4-(4-tert-butyldimethylsilyloxyphenyl)-1-methyl-3-[4-(2-chloroethyloxy)phenyl]-bicyclo[4.3.0]non-3-ene The solution of the crude product, presented according to Example 14e, in a mixture of 150 ml of toluene and 66 ml of ethanol is mixed under an atmosphere of argon with 955 mg of lithium chloride, 15 ml of a 2 M sodium carbonate solution, 1.0 g of [4-(2-chloroethyloxy)phenyl]-boronic acid, 1.0 g of tetrakis-triphenylphosphine-palladium (O), and it is heated for 1.5 hours to 95° C. It is diluted with water, extracted several times with ethyl acetate, and the combined organic extracts are dried on sodium sulfate. The residue that is obtained after filtration and removal of the solvent is purified by chromatography on about 1.5 l of fine silica gel with a gradient system that consists of n-hexane and ethyl acetate. 2.15 g (3.43 mmol, 34% relative to the starting material in Example 14e) of the title compound is isolated as a colorless foam as well as 1.82 g of the title compound that is mentioned in Example 14d.

$^1$H-NMR (CDCl$_3$): δ=0.02 (6H), 0.12 (6H), 0.86 (3H), 0.89 (9H), 0.92 (9H), 1.32–1.81 (5H), 1.89–2.54 (4H), 3.69–3.85 (3H), 4.13 (2H), 6.57 (2H), 6.63 (2H), 6.80 (2H), 688 (2H) ppm.

Example 14g (1S,4S,6S,9S)-4-(4-Hydroxyphenyl)-1-methyl-3-oxo-bicyclo[4.3.0]nonan-9-ol 940 mg (1.92 mmol) of the compound that is presented according to Example 14d or recovered from Example 14f is reacted analogously to Example 14 (variant I), and after working-up and purification, 415 mg (1.59 mmol, 83%) of the title compound is isolated as a colorless foam.

Example 14h (1S,4S,6S,9S)-1-Methyl-3-oxo-9-(tetrahydropyran-2-yloxy)-4-[4-(tetrahydropyran-2-yloxy)phenyl]-bicyclo[4.3.0]nonane The solution of 415 mg (1.59 mmol) of the compound, presented according to Example 14g, in 10 ml of anhydrous dichloromethane is mixed under an atmosphere of dry argon with 0.73 ml of 3,4-dihydro-2H-pyran, 80 mg of p-toluenesulfonic acid-pyridinium salt, and it is stirred for 16 hours at 23° C. It is mixed with saturated sodium bicarbonate solution, extracted several times with dichloromethane, the combined organic extracts are washed with saturated sodium chloride solution and dried on sodium sulfate. The residue that is obtained after filtration and removal of the solvent is purified by chromatography on about 300 ml of fine silica gel with a gradient system that consists of n-hexane and ethyl acetate. 548 mg (1.27 mmol, 81%) of the title compound is isolated as a colorless foam.

$^1$H-NMR (CDCl$_3$): δ=0.87+0.89 (3H), 1.39–2.30 (19H), 2.38 (1H), 2.62+2.73 (1H), 3.36–3.65 (3H), 3.78–4.01 (3H), 4.61+4.68 (1H), 5.41 (1H), 7.03 (4H) ppm.

Example 14i (1S,6S,9S)-1-Methyl-3-(nonafluorobutylsulfonyloxy)-9-(tetrahydropyran-2-yloxy)-4-[4-(tetrahydropyran-2-yloxy)phenyl]-bicyclo[4.3.0]non-3-ene 543 mg (1.27 mmol) of the compound that is presented according to Example 14h is reacted analogously to Example 14e, and the crude product that is obtained after working-up is further reacted without purification.

Example 14k (1S,6S,9S)-9-(Tetrahydropyran-2-yloxy)-4-[4-(tetrahydropyran-2-yloxy)phenyl]-1-methyl-3-[4-(2-chloroethyloxy)phenyl]-bicyclo [4.3.0]non-3-ene The crude product that is presented according to Example 14i is reacted analogously to Example 14f, and after working-up and purification, 181 mg (0.32 mmol, 25% relative to the starting material in Example 14i of the title compound is isolated as a colorless foam as well as 350 mg of the title compound that is mentioned in Example 14h.

Example 14

(1S,6S,9S)-9-Hydroxy-4-(4-hydroxyphenyl)-1-methyl-3-[4-(2-chloroethyloxy)phenyl]-bicyclo [4.3.0]non-3-ene Variant I The solution of 2.14 g (3.42 mmol) of the compound, presented according to Example 14f, in 100 ml of acetone is mixed with 5 ml of a 4N hydrochloric acid, and it is stirred under argon atmosphere for 1 hour at 23° C. It is mixed with saturated sodium bicarbonate solution, extracted several times with dichloromethane, and the combined organic extracts are dried on sodium sulfate. The residue that is obtained after filtration and removal of the solvent is purified by chromatography on about 300 ml of fine silica gel with a gradient system that consists of n-hexane and ethyl acetate. 642 mg (1.16 mmol, 34%) of the title compound is isolated as a colorless foam.

Variant II 181 mg (0.32 mmol) of the compound that is presented according to Example 14k is reacted analogously to Example 14 (variant I), and after working-up and purification of the title compound is isolated as a colorless foam.

$^1$H-NMR (CDCl$_3$): δ=0.92 (3H), 1.34–1.90 (6H), 2.09–2.58 (5H), 3.77 (2H), 3.88 (1H), 4.13 (2H), 6.58 (2H), 6.66 (2H) 6.83 (2H), 6.89 (2H) ppm.

Example 15

(1S,6S,9S)-9-Hydroxy-4-(4-Hydroxyphenyl)-1-methyl-3-[4-(2-(dimethylamino)ethyloxy)phenyl]-bicyclo[4.3.0]non-3-ene 10 ml of ethanol is saturated with dimethylamine, mixed with the solution of 637 mg (1.60 mmol) of the compound, presented according to Example 14, in 5 ml of ethanol, and it is stirred for 2.5 days at 80° C. under an atmosphere of dry argon. It is mixed with water, a 5% sodium hydroxide solution, extracted several times with trichloromethane, and the combined organic extracts are dried on sodium sulfate. After filtration and removal of the solvent, 584 mg (1.43 mmol, 90%) of the title compound is isolated as a colorless foam.

$^1$H-NMR (CDCl$_3$): δ=0.91 (3H), 1.23–1.64 (3H), 1.70–1.89 (2H), 2.00 (1H), 2.09–2.57 (5H), 2.49 (6H), 2.79 (2H), 3.88 (1H), 4.01 (2H), 6.55 (2H), 6.58 (2H), 6.79 (2H), 6.86 (2H) ppm.

Example 16

(1S3S,4R,6S,9S)-9-Hydroxy-4-(4-hydroxyphenyl)-1-methyl-3-[4-(2-(dimethylamino)ethyloxy)phenyl]-bicyclo[4.3.0]nonane The solution of 100 mg (0.245 mmol) of the compound, presented according to Example 15, in 4 ml of ethanol is mixed in portions with a total of 70 mg of palladium on carbon (10%), and it is hydrogenated for 10 days at 200 bar. After filtration, the crude product is purified chromatographically. 67 mg (165 μmol, 67%) of the title compound is isolated as a colorless foam.

$^1$H-NMR (CDCl$_3$/CD$_3$OD): δ=0.32 (3H), 1.28–1.69 (4H), 1.78 (1H), 1.98–2.17 (3H), 2.32 (1H), 2.81 (6H), 3.09 (1H), 3.32 (2H), 3.57–3.73 (2H), 4.10 (2H), 6.49 (2H), 6.65 (2H), 7.03 (2H), 7.11 (2H) ppm.

Example 17

(1S,3S,4R,6S,9)-9-Acetyloxy-4-(4-hydroxyphenyl)-1-methyl-3-[4-(10,10,11,11,11-pentafluoropentylsulfonyl)pentyloxy)phenyl]-bicyclo[4.3.0]nonane 250 mg (0.389 mmol) of the compound that is presented according to Example 2 is reacted analogously to Example 3, and after working-up and purification, 144 mg (0.213 mmol, 55%) of the title compound is isolated as a colorless solid.

$^1$H-NMR (CDCl$_3$): δ=0.44 (3H), 1.40–1.81 (8H), 1.82–1.97 (3H), 2.00 (3H), 2.08–2.38 (8H), 2.90–3.09 (4H), 3.14 (1H), 3.70 (1H), 3.85 (2H), 4.63 (1H), 4.73 (1H), 6.57 (2H), 6.69 (2H), 7.02 (2H), 7.18 (2H) ppm.

Example 18

(1S,3S,4R,6S,9S)-9-Hydroxy-4-(4-hydroxyphenyl)-1-methyl-3-[4-(2-chloroethyloxy)phenyl]-bicyclo [4.3.0]nonane 50 mg (0.125 mmol) of the compound that is presented according to Example 14 is reacted analogously to Example 1m, and after working-up and purification, 41 mg (0.102 mmol, 82%) of the title compound is isolated as a colorless foam.

$^1$H-NMR (CDCl$_3$/CD$_3$OD): δ=0.31 (3H), 1.29–1.68 (4H), 1.76 (1H), 1.95–2.17 (3H), 2.36 (1H), 3.09 (1H), 3.56–3.75 (2H), 3.70 (2H), 4.07 (2H), 6.56 (2H), 6.65 (2H), 7.02 (2H), 7.12 (2H) ppm.

Example 19

(1S,3S,4R,6S,9S)-3-[4-(5-Chloropentyloxy)phenyl]-3,4-epoxy-9-hydroxy-4-(4-hydroxyphenyl)-1-methyl-bicyclo[4.3.0]nonane 1.00 g (2.27 mmol) of the compound that is presented according to Example 6b is reacted analogously to Example 3, and after working-up and purification, 597 mg (1.31 mmol, 58%) of the title compound is isolated as a colorless foam.

$^1$H-NMR (CDCl$_3$/CD$_3$OD): δ=1.07 (3H), 1.32–2.22 (15H), 2.33 (1H), 3.50 (2H), 3.70 (1H), 3.79 (2H), 6.51 (2H), 6.56 (2H), 6.92 (2H), 6.98 (2H) ppm.

Example 20

(1S,3S,4R,6S,9S)-3-[4-(10,10,11,11,11-pentafluoro-6-thia-undecyloxy)phenyl]-3,4-epoxy-9-hydroxy-4-(4-hydroxyphenyl)-1-methyl-bicyclo[4.3.0]nonane (A) and (1S,3S,6S,9S)-3-[4-(10,10,11,11,11-pentafluoro-6-thia-undecyloxy)phenyl]-3,9-dihydroxy-4-(4-hydroxyphenyl)-1-methyl-bicyclo[4.3.0]non-4-ene (B)

592 mg (1.30 mmol) of the compound that is presented according to Example 19 is reacted analogously to Example 1, and after working-up and purification, 259 mg (0.42 mmol, 32%) of title compound A is isolated respectively as a colorless foam, and after purification, 140 mg (0.23 mmol, 18%) of title compound B is isolated respectively as a colorless foam.

$^1$H-NMR (CDCl$_3$) of A: δ=1.12 (3H), 1.34–1.76 (10H), 1.78–2.27 (9H), 2.38 (1H), 2.51 (2H), 2.59 (2H), 3.80 (1H) 3.83 (2H), 4.68 (1H), 6.55 (2H), 6.61 (2H), 7.00 (4H) ppm.

$^1$H-NMR (CDCl$_3$) of B: δ=0.70 (3H), 1.34 (1H), 1.45–1.94 (11H), 2.02–2.28 (5H), 2.39–2.64 (6H), 3.87 (1H), 3.90 (2H) 4.81 (1H), 6.23 (1H), 6.61 (2H), 6.71 (2H), 7.29 (4H) ppm.

Example 21

(1S,3S,4R,6S,9S)-3-[4-(5-(4,4,5,5,5-pentafluoro-pentylsulfonyl)pentyloxy)phenyl-3,4-epoxy-9-hydroxy-4-(4-hydroxyphenyl)-1-methyl-bicyclo[4.3.0]nonane 149 mg (0.24 mmol) of the compound that is presented according to Example 20 is reacted analogously to Example 3, and after working-up and purification, 64 mg (0.10 mmol, 42%) of the title compound is isolated as a colorless foam.

$^1$H-NMR (CDCl$_3$): δ=1.11 (3H), 1.33–1.76 (10H), 1.80–2.33 (9H), 2.41 (1H), 2.53–2.88 (4H), 3.80 (1H), 3.89–4.04 (2H), 6.52 (2H), 6.59 (2H), 6.90 (2H), 7.00 (2H), 7.170+7.26 (1H) ppm.

Example 22

(1S,3S,4R,6S,9S)-9-Hydroxy-4-(4-hydroxyphenyl)-1-methyl-3-[4-(2-(pentamethylenamino)ethyloxy)phenyl]-bicyclo[4.3.0]nonane The solution of 31 mg (77 μmol) of the compound that is presented according to Example 18 is reacted analogously to Example 15 using piperidine, and after working-up and purification, 24 mg (53 μmol, 69%) of the title compound is isolated as a pale yellow foam.

$^1$H-NMR (CDCl$_3$/CD$_3$OD): δ=0.33 (3H), 1.28–1.70 (11H), 1.77 (1H), 1.98–2.18 (3H), 2.35 (1H), 2.55 (4H), 2.74 (2H) 3.09 (1H), 3.58–3.74 (2H), 3.96 (2H), 6.52 (2H), 6.66 (2H) 7.01 (2H), 7.12 (2H) ppm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A method for treating anovulatory infertility, melanoma, estrogen depletion in peri- or post-menopausal women, hormone-dependent tumors, male hair loss, alopecia, hirsutism, endometriosis, or osteoporosis, or to effect male or female birth control, or to perform hormone replacement therapy, comprising administering to a patient in need of such treatment an effective dose of a 3,4-diphenyl- bicyclo[4.3.0]nonyl compound of formula I:

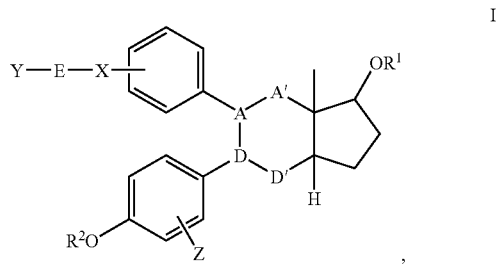

in which

R$^1$ is optionally substituted C$_1$–C$_{20}$ alkanoyl, optionally substituted C$_1$–C$_{20}$ alkyl, optionally substituted C$_7$–C$_{20}$ aralkyl, optionally substituted C$_7$–C$_{15}$ aroyl, a group PG$^1$ or a hydrogen atom, R$^2$ is optionaliy substituted C$_1$–C$_{20}$ alkanoyl, optionally substituted C$_1$–C$_{20}$ alkyl, optionally substituted C$_7$–C$_{20}$ aralkyl, optionally substituted C$_7$–C$_{15}$ aroyl, a group PG$^2$ or a hydrogen atom, PG$^1$ and PG$^2$ are the same or different and each is a protective group PG, A'—A—D—D' is a —CH$_2$—CH(OH)—CH=CH—, —CH=CH—CH(OH)—CH$_2$—, —CH=CH—CH=CH—, —CH$_2$—CH=CH—CH$_2$—, —CH$_2$—CH(OH)—CH$_2$—CH$_2$—, —CH$_2$—CH$_2$—CH$_2$—CH$_2$—, —CH$_2$—CH$_2$—CH(OH)—CH$_2$—, —CH$_2$—CH(OH)—CH(OH)—CH$_2$— or

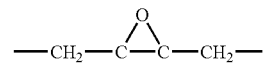

group, where the hydroxy groups can be α or β, and the epoxy group can be α or β, X is a bond, an oxygen atom, a sulfur atom, SO or SO$_2$, E is a straight-chain or branched-chain alkylene, alkenylene or alkynylene group with 1 to 15 carbon atoms, Y is F, Cl, Br, I, a substituent $R^4$, an optionally substituted aryl or heteroaryl radical, or an $NR^{4a}R^{4b}$—, $SO_2NR^{4a}R^{4b}$—, $NR^{4a}(CH_2)_p$-Q-G-, $NR^5(CHR^{6-}CHR^7)$—$(CH_2)_t$-Q-G-, $SO_2NR^{4a}(CH_2)_p$-Q-G-, O-G-, S-G-,SO-G-, or $SO_2$-G group, $R^4$ is a hydrogen atom, optionally substituted $C_1$–$C_{20}$ alkyl, partially or completely fluorinated $C_1$–$C_{20}$ alkyl, optionally substituted $C_1$–$C_{20}$ alkanoyl, optionally substituted aryl, optionally substituted heteroaryl, optionally substituted $C_7$–$C_{20}$ aralkyl, or optionally substituted $C_7$–$C_{15}$ aroyl, Q is an oxygen atom, a sulfur atom, SO or $SO_2$, G is —$(CH_2)_n$—$R^3$, n is 0 to 10, p is 1 to 10, t is 0, 1 or 2, $R^3$ is hydrogen, a straight-chain or branched-chain alkyl, alkenyl or alkynyl group with up to 10 carbon atoms, a straight-chain or branched-chain, partially or completely fluorinated, alkyl or alkenyl group with up to 10 carbon atoms, an optionally substituted $C_4$–$C_8$ cycloalkyl group, an optionally substituted aryl group, an optionally substituted $C_7$–$C_{20}$ aralkyl group or, if n>0, a hydroxy group or a halogen atom, $R^{4a}$ and $R^{4b}$ are the same or different as defined for $R^4$ or together are a $C_3$–$C_{15}$ alkylene group, which can be straight-chain or branched, $R^5$ is a hydrogen atom or a $C_1$–$C_5$ alkyl group, $R^6$ and $R^7$ each is a hydrogen atom, or $R^5$ and $R^6$ together are an alkylene group —$(CH_2)_d$— with d=2, 3, 4 or 5 and $R^7$ is a hydrogen atom, or $R^5$ and $R^7$ together are an alkylene group —$(CH_2)_e$— with e=2, 3 or 4 and $R^6$ is a hydrogen atom, and Z is hydrogen, halogen, OH, $N_3$, $NH_2$, $CO_2H$, $CO_2$—$(C_1$–$C_{20})$-alkyl, $C_1$–$C_{20}$ alkoxy, —$NO_2$, —CN or $C_1$–$C_{20}$ acyloxy.

2. A method of claim 1, wherein in the compound of formula I, $R^1$ and/or $R^2$ is a hydrogen atom.

3. A method of claim 1, wherein in the compound of formula I, A'—A—D—D' is a —$CH_2$—$CH_2$—$CH_2$—$CH_2$— group.

4. A method of claim 1, wherein in the compound of formula I, A'—A—D—D' is a —$CH_2$—CH=CH—$CH_2$— group.

5. A method of claim 1, wherein in the compound of formula I,

A'—A—D—D' is a

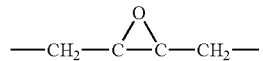

group, where the epoxy is an α epoxy.

6. A method of claim 1, wherein in the compound of formula I, A'—A—D—D' is a —$CH_2$—CH(OH)—CH=CH— group.

7. A method of claim 1, wherein in the compound of formula I, side chain -X-E-Y is

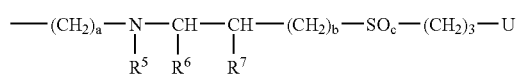

wherein a is 4, 5 or 6, b is 0, 1 or 2, c is 0, 1 or 2, $R^5$ is a hydrogen atom or a $C_1$–$C_5$ alkyl group, $R^6$ and $R^7$ are each a hydrogen atom, or $R^5$ and $R^6$ together are an alkylene group —$(CH_2)_d$— with d=2, 3, 4 or 5, and $R^7$ is a hydrogen atom or $R^5$ and $R^7$ together are an alkylene group —$(CH_2)_e$— with e=2, 3 or 4, and $R^6$ is a hydrogen atom, and U is an unsubstituted ethyl radical or an ethyl radical that is fluorinated in one to five places, or the terminal substituent —$(CH_2)_3$—U in the side chain is replaced by an optionally substituted aryl or heteroaryl radical, which is bonded to the sulfur atom directly or via a mono-, di- or trimethylene group.

8. A method of claim 7, wherein in the compound of formula I, -X-E-Y is the side chain —$(CH_2)_5N(CH_3)(CH_2)_3S(CH_2)_3C_2F_5$.

9. A method of claim 7, wherein in the compound of formula I, -X-E-Y is the side chain

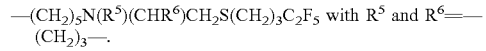

10. A method of claim 1, wherein in the compound of the formula I, $R^1$ and/or $R^2$ is PG, where PG is methoxymethyl, methoxyethyl, ethoxyethyl, tetrahydropyranyl, tetrahydrofuranyl, trimethylsilyl, triethylsilyl, tert-butyldimethylsilyl-, tert-butyldiphenylsilyl, tribenzylsilyl, triisopropylsilyl, methyl, tert-butyl, benzyl, para-nitrobenzyl, para-methoxybenzyl, formyl, acetyl, propionyl, isopropionyl, pivalyl, butyryl, or benzoyl.

11. The method of claim 1, further comprising administering an antigestagen.

12. The method of claim 1, wherein the patient is human.

13. The method of claim 1, wherein the dose of compound of the formula I is 50 to 200 mg daily.

14. The method of claim 1, wherein the compound is administered orally.

15. The method of claim 1, wherein the compound is administered parenterally.

16. The method of claim 1, wherein in formula I:

the optional substituents for $C_1$–$C_{20}$ alkyl, $C_1$–$C_{20}$ alkanoyl, or $C_4$–$C_8$ cycloalkyl are 1–10 halogen atoms, hydroxy groups, $C_1$–$C_4$ alkoxy groups, or $C_1$–$C_{12}$ aryl groups, which aryl groups are optionally substituted by 1–3 halogen atoms, di-$(C_1$–$C_4)$alkylamines or tri-$(C_1$–$C_4)$-alkylammonium;

the optional substituents for $C_7$–$C_{20}$ aralkyl are, in one or more places, halogen, OH, O-alkyl, $CO_2H$, $CO_2$ alkyl, —$NO_2$, —$N_3$, —CN, $C_1$–$C_{20}$ alkyl, $C_1$–$C_{20}$ acyl, or $C_1$–$C_{20}$ acyloxy groups;

the optional substituents for aryl, $C_7$–$C_{15}$ aroyl, or heteroaryl are halogens, OH, $C_1$–$C_{20}$ alkoxy, $CO_2H$, $CO_2$ alkyl, —$NO_2$, —$N_3$, —CN, $C_1$–$C_{20}$ alkyl, $C_{1-C20}$ acyl, or $C_1$–$C_{20}$ acyloxy;

$C_7$–$C_{20}$ aralkyl has 1 to 14 C atoms in the ring and 1 to 8 C atoms in the alkyl;

aryl is a structure with 1 or 2 rings and 3 to 10 C atoms, and heteroaryl is such a structure which additionally contains one or more N, S or O atoms in place of C; and heteroaryl is a $C_4$–$C_{10}$ ring which optionally contains one or more N, S or O atoms in place of C.

* * * * *

UNITED STATES PATENT AND TRADEMARK OFFICE
CERTIFICATE OF CORRECTION

PATENT NO. : 7,074,829 B2
APPLICATION NO. : 10/369577
DATED : July 11, 2006
INVENTOR(S) : Klar et al.

It is certified that error appears in the above-identified patent and that said Letters Patent is hereby corrected as shown below:

Column 29, line 54 reads "C-C" should read -- CH-CH --
Column 30, line 57 reads "c20" should read -- C20 --

Signed and Sealed this

Twelfth Day of December, 2006

JON W. DUDAS
*Director of the United States Patent and Trademark Office*